United States Patent
Jepson et al.

(10) Patent No.: US 12,146,010 B2
(45) Date of Patent: Nov. 19, 2024

(54) AMINE CO-INITIATOR MIXTURE

(71) Applicant: Arkema UK Limited, Stafford (GB)

(72) Inventors: David Jepson, Wetherby (GB); Richard Plenderleith, Wetherby (GB); Kelly Squires, Wetherby (GB); Andrew Towns, Wetherby (GB); Petr Sehnal, Wetherby (GB)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 17/768,521

(22) PCT Filed: Oct. 16, 2020

(86) PCT No.: PCT/EP2020/079157
§ 371 (c)(1),
(2) Date: Apr. 13, 2022

(87) PCT Pub. No.: WO2021/074363
PCT Pub. Date: Apr. 22, 2021

(65) Prior Publication Data
US 2024/0141078 A1    May 2, 2024

(30) Foreign Application Priority Data
Oct. 17, 2019    (GB) .................. 1915023.4

(51) Int. Cl.
C08F 2/50    (2006.01)
C07C 229/60    (2006.01)
C09D 11/101    (2014.01)

(52) U.S. Cl.
CPC ............. *C08F 2/50* (2013.01); *C07C 229/60* (2013.01); *C09D 11/101* (2013.01)

(58) Field of Classification Search
None
See application file for complete search history.

(56) References Cited

U.S. PATENT DOCUMENTS

| 6,117,612 A | 9/2000 | Halloran et al. |
| 2014/0315002 A1 | 10/2014 | Gaudl et al. |
| 2016/0208117 A1 | 7/2016 | Loccufier et al. |

FOREIGN PATENT DOCUMENTS

| JP | 2014227344 A2 | 12/2014 |
| JP | WO15072415 A1 | 5/2015 |

OTHER PUBLICATIONS

A. Green, "Industrial Photoinitiators: A Technical Guide", Taylor and Francis Group 2010, p. 70).

Chem Rev 2010, 110, pp. 5845-5882—"Toward a Comprehensive Molecular Design Framework for Reduced Hazard", Voutchkova, Osimitz and Anastas—2010 American Chemical Society—Published on Web Sep. 27, 2010.
CRC Press Taylor & Francis Group—Library of Congress Catalogs in Publication Data—International Standard Book No. 978-1-4398-2745-1 (paperback).
L.L. Katon—p. 97.
L.L.Katon Copyright Page—Published by Blackie Academic & Professional, An Imprint of Chapman & Hall.
"Low Extractable/Low Odor Acrylates for Food Packing Applications" V. Stone et al—Cytec Specialty Chemicals RadTech e/5 2006 Technical Proceedings.

*Primary Examiner* — Sanza L. McClendon
(74) *Attorney, Agent, or Firm* — Christopher R. Lewis

(57) ABSTRACT

The invention relates to a co-initiator comprising the aminobenzoate derivative according to Formula (I) and at least one ancillary amine, wherein the reactivity and solubility of said co-imitator in UV-curable resins is sufficiently high that the co-initiator can be used in UV radiation curing processes. Formula (I) wherein $R^1$ and $R^2$ independently represent methyl or ethyl groups; and j, k, l and m are independently 0 to 20.

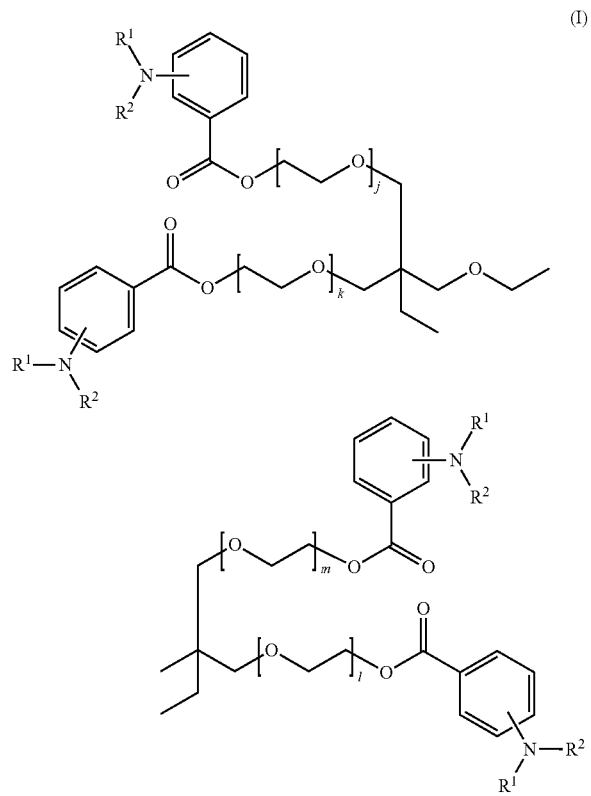

24 Claims, 2 Drawing Sheets

AMINE CO-INITIATOR MIXTURE

CROSS-REFERENCE TO RELATED APPLICATIONS

This application is a U.S. national stage application under 35 U.S.C. § 371 of international application number PCT/EP2020/079157, filed Oct. 16, 2020, which claims priority to patent application number GB 1915023.4, filed Oct. 17, 2019.

FIELD OF THE INVENTION

The invention relates to an amine co-initiator mixture comprising at least two amines, in particular to an amine co-initiator comprising an aminobenzoate compound as a first component. These co-initiators may be used in coatings and inks.

BACKGROUND OF THE INVENTION

Radiation-curable compositions containing acrylate esters and other similar unsaturated compounds can be polymerised by exposure to ultraviolet (UV) light. For rapid, effective curing a photoinitiator is often necessary, which forms radical species upon irradiation with photons and initiates free-radical polymerisation of unsaturated groups, leading to hardening (curing) of the material.

Unlike Type-I photoinitiators—which cleave upon exposure to UV radiation, producing radical species which are capable of initiating the polymerisation of unsaturated compounds—so-called Type-II photoinitiators (not to be confused with the Norrish Type-II reaction, which involves intramolecular hydrogen abstraction of a biradical species) are compounds which do not fragment upon exposure to UV radiation and so will not typically initiate radical-chain polymerisation unless a further co-initiator is present. Interaction between Type-II photoinitiators and appropriate co-initiators upon exposure to UV radiation leads to the generation of radical species which can initiate the polymerisation of UV-curable resins.

Suitable Type-II photoinitiators include diaryl ketones such as benzophenone (e.g. SpeedCure BP—Lambson Limited) or thioxanthones such as 2-isopropylthioxanthone (e.g. SpeedCure 2-ITX—Lambson Limited). Suitable co-initiators can include thiols or, more commonly, tertiary amines. Tertiary amines are especially useful for the surface cure of UV-inks and UV-coatings as they are able to react with otherwise inactive peroxy radicals, which are formed upon reaction between radical species and atmospheric oxygen, to give more reactive species that are able to continue the polymerisation reaction, thus reducing the inhibiting effect of oxygen on the surface of inks and coatings (A. Green, "Industrial Photoinitiators: A Technical Guide", Taylor and Francis Group 2010, Page 70).

Radiation-curable compositions containing photoinitiators, co-initiators and other additives can be problematic in packaging applications, especially in food packaging ("Radiation Curing in Packaging", Radtech Report March/April 2006). Residual photoinitiators, co-initiators and other additives, as well as their fragmentation products, may migrate out of the coating or ink if they are not chemically-bound to the polymer backbone. This can lead to the contamination of any adjacent materials, and in the case of foodstuffs may lead to problems with off-taste and odour. There is therefore a continuous search for photoactive compounds which have low potential for migration. In some cases there may also be problems with the toxicity of some of these molecules or their fragmentation products, so the development of low-toxicity additives is also important.

A diffusion-hindered photoinitiator or co-initiator is a photoactive molecule which exhibits low mobility in a cured layer of the curable composition or ink, thus reducing its propensity to migrate. As described in the literature (L. L. Katan, "Migration from Food Contact Materials", Blackie Academic and Professional, $1^{st}$ Ed. London 1996) the ability of a molecule to migrate is often determined by its molecular weight. Therefore, for a low migration UV-curable ink or coating, photoactive components having a molecular weight of greater than 500 Daltons are preferred. Likewise, the toxicity of any photoactive components is likely to be lower when said molecules are higher molecular weight owing to their reduced bioavailability; generally molecules that have a molecular weight of greater than 500 Daltons are preferred because they are not likely to be absorbed into the skin or through the gastrointestinal tract (Voutchkova et al, *Chem. Rev.* 2010, 110, 5845-5882).

Among the most reactive tertiary amines employed as co-initiators for Type-II photoinitiators are aminobenzoate derivatives such as ethyl 4-(dimethylamino)benzoate (e.g. SpeedCure EDB—Lambson Limited) and 2-ethylhexyl-4-(dimethylamino)benzoate (e.g. SpeedCure EHA—Lambson Limited). Such aminobenzoate derivatives are especially useful in lithographic ink formulations in which the water balance of the inks is critical to their application, and where more hydrophilic tertiary amines might not be suitable. In cases where higher concentrations of the amine are used in order to reduce oxygen inhibition, migration is more likely to occur since a proportion of the amine co-initiator may remain unreacted and therefore not chemically-bound to the polymer backbone. Due to the toxicological classification of these compounds, migration has the potential to be harmful to health.

The use of multifunctional amine co-initiators increases the likelihood that the co-initiator will be chemically-bound to the polymer backbone after curing, thus reducing the likelihood that the co-initiator molecule will migrate. For multifunctional amine co-initiators with high molecular weights, particularly those with molecular weights of >500 Daltons, migration of any unreacted co-initiator would also be diffusion-hindered. Among the high molecular weight, diffusion-hindered co-initiators already available for low migration applications are oligomeric aminobenzoates such as Omnipol ASA (IGM Resins) and SpeedCure 7040 (Lambson Limited), but these substances are less photoactive than their small-molecule counterparts, and can often suffer from solubility issues. There is therefore a continuing need to discover new high molecular weight, diffusion-hindered tertiary amine co-initiators which exhibit the properties of low migration and low toxicity while also being highly active with good solubility.

SUMMARY OF THE INVENTION

In a first aspect of the invention, there is provided a high molecular weight, diffusion-hindered amine co-initiator mixture comprising amine derivatives including the aminobenzoate derivative according to Formula I, shown below, along with one or more ancillary amines as defined in claim 1. The mixtures exhibit high co-initiator efficiency in the presence of Type-II photoinitiators for initiating UV curing and, surprisingly, are sufficiently soluble in a range of acrylate resins across a suitable range of concentrations. Furthermore, the solubility of the co-initiator mixture in acrylate resins is often higher than that of individual multifunctional amine co-initiators when they are not present in such a mixture.

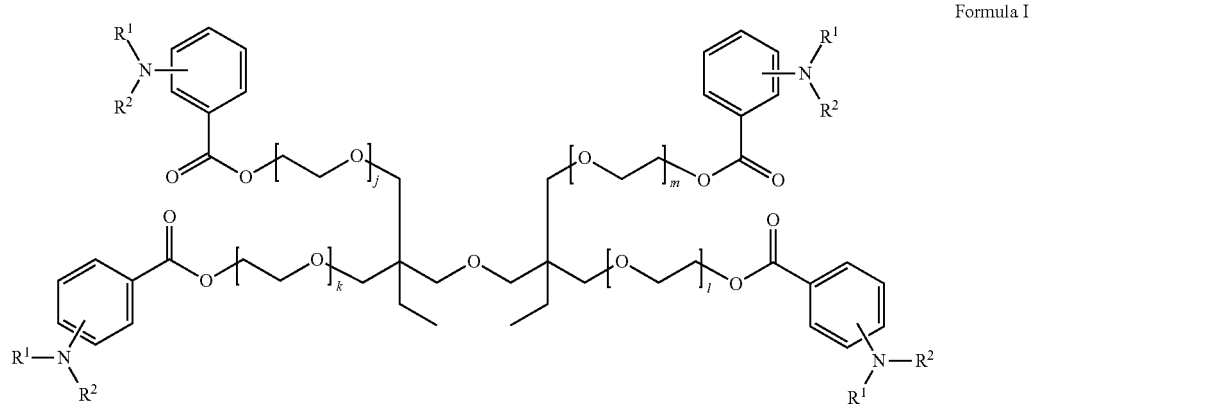

Formula I wherein $R^1$ and $R^2$ independently represent methyl or ethyl groups; and j, k, l and m independently represent integers from 0 to 20.

Illustrations of the present invention are described herein.

The present invention relates to amine co-initiator mixtures for use in compositions which are curable with ultraviolet light. More specifically, the co-initiator mixture is suitable for applications in which the properties of low migration, low toxicity and high solubility (in particular in acrylate resins) are especially desirable.

BRIEF DESCRIPTION OF THE DRAWING

In order that the invention may be more readily understood, it will be described further with reference to the figures and to the specific examples provided herein.

DETAILED DESCRIPTION OF THE INVENTION

Figure 1:
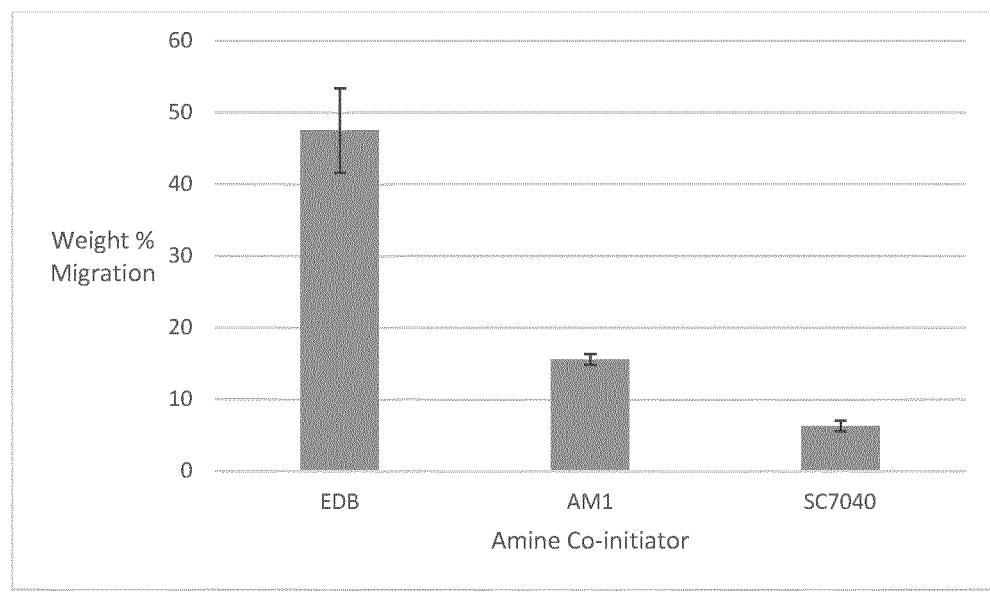
FIG. 1 illustrates the migration of amine co-initiators (the amines SpeedCure EDB and SpeedCure 7040, and mixture AM1) into acetonitrile, 60° C. for 10 days, average of three runs (standard deviations included).

The invention seeks to provide effective multifunctional, diffusion-hindered co-initiator mixtures which are especially useful for low migration coatings and inks and which exhibit good solubility in the polymerisable resin system. This is achieved through the provision of co-initiator mixtures, comprising the aminobenzoate compound according to Formula I, along with one or more ancillary amines.

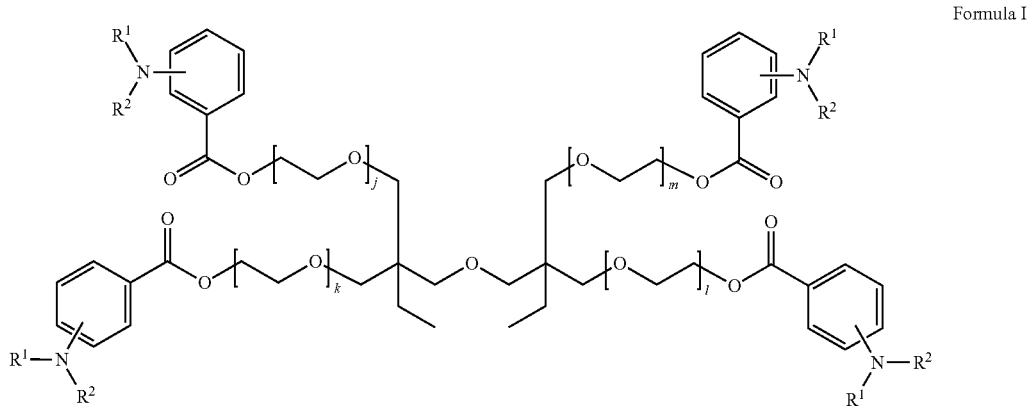

Formula I wherein $R^1$ and $R^2$ independently represent methyl or ethyl groups; and j, k, l and m independently represent integers from 0 to 20.

Often, at least one of $R^1$ or $R^2$ will be methyl, in some cases both $R^1$ and $R^2$ will be methyl as methyl groups have been found to offer the greatest activity. In some cases the N,N-dialkylamino groups (—$NR^1R^2$) in Formula I are at the 4-position (para) with respect to the ester groups, although they may also be at the 2-position (ortho), or the 3-position (meta), for synthetic reasons positioning at the 2- or 4-position is often selected, with the 4-position being most common. Further, the N,N-dialkylamino groups may be in different positions on different rings, for instance, the N,N-dialkylamino groups may be in the 4-position on 1, 2, or 3 rings, although often the positioning of the N,N-dialkylamino groups will be the 4-position for all 4 rings. There will generally be only a single N,N-dialkylamino group on each ring as illustrated.

In one embodiment, the compound of formula I may have j, k, l and m that are all equal to 0.

In another embodiment, the compound of formula I may be an ethoxylated compound. As used herein, the term "ethoxylated compound" means a compound having one or more oxyethylene —[O—$CH_2$—$CH_2$]— units. Accordingly, the compound of formula I may have at least one of j, k, l and m that is not equal to 0. In particular, the sum of j+k+l+m may be from 1 to 30, from 4 to 25, or from 6 to 20. More particularly, j, k, l and m independently represent integers from 0 to 20, from 1 to 10 or from 2 to 5.

In a particularly preferred example, the co-initiator according to Formula I has the structure according to Formula I-a.

group that may have a beneficial effect on the compound of formula (I). For example, the ancillary amine may enhance the solubility and/or curing efficiency of the compound of formula (I).

In a preferred example, the ancillary amine in the co-initiator mixture is an aminobenzoate derivative, often this will be a tertiary amine, such as a N,N-dialkylaminobenzoate derivative. In one embodiment, the ancillary amine comprises at least one, in particular at least 2, more particularly at least 3, aminobenzoate moieties. In particular, the ancillary amine may comprise 2 to 6 aminobenzoate moieties. In particular, the amino group of the aminobenzoate moiety may be a tertiary amino group.

In one embodiment, the ancillary amine comprises at least one, in particular at least two, more particularly at least three, N,N-dialkylaminobenzoate moieties. In particular, the ancillary amine may comprise 2 to 6 N,N-dialkylaminobenzoate moieties. As used herein, the term "N,N-dialkylaminobenzoate moiety" means a group of formula (A):

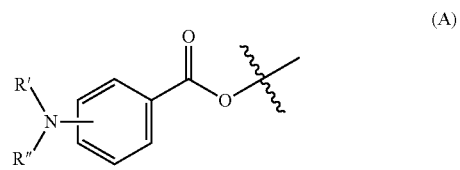

wherein R' and R" are independently alkyl, in particular methyl or ethyl, more particularly methyl.

Formula I-a

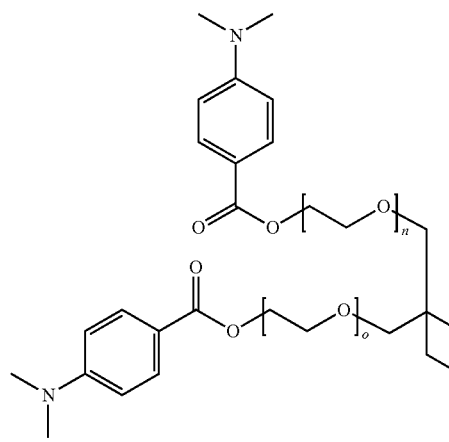
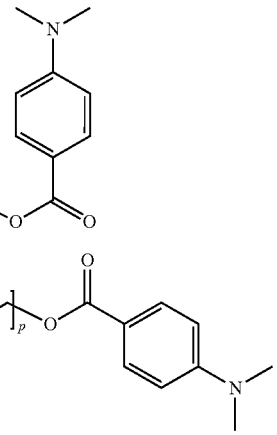

wherein n, o, p and q independently represent integers from 0 to 20.

In one embodiment, the compound of formula I-a may have n, o, p and q that are all equal to 0.

In another embodiment, the compound of formula I-a may be an ethoxylated compound. Accordingly, the compound of formula I-a may have at least one of n, o, p and q that is not equal to 0. In particular, the sum of n+o+p+q may be from 1 to 30, from 4 to 25, or from 6 to 20. More particularly, n, o, p and q may independently represent integers from 0 to 20, from 1 to 10 or from 2 to 5.

The co-initiator mixture of the present invention comprises an ancillary amine. As used herein, the term "ancillary amine" means a compound comprising at least one amine In particular, the N,N-dialkylaminobenzoate moiety of formula (A) may have the N,N-dialkylamino group (—NR'R") in the 4-position (para) with respect to the ester group.

The ancillary amine may have 1, 2, 3, 4, 5 or 6 N,N-dialkylaminobenzoate moieties wherein the N,N-dialkylamino group is in the 4-position with respect to the ester group. The ancillary amine may also have N,N-dialkylaminobenzoate moieties wherein the N,N-dialkylamino group is in the 2-position (ortho) or 3-position (meta) with respect to the ester group. More particularly, all of the aminobenzoate moieties of the ancillary amine have the N,N-dialkylamino group in the 4-position.

The structure of the ancillary amine will be different to that of the compound of Formula I, although there may be more than one compound of structural Formula I present in the co-initiator. In addition, there may be more than one ancillary amine present in the co-initiator, in particular there may be one or more compounds of formulae II-III as described below, additionally or alternatively to the compounds present in Table 1.

In a particularly preferred example the compound according to Formula I is present in a mixture with the ancillary amine according to Formula II, also a co-initiator, including any stereoisomers thereof.

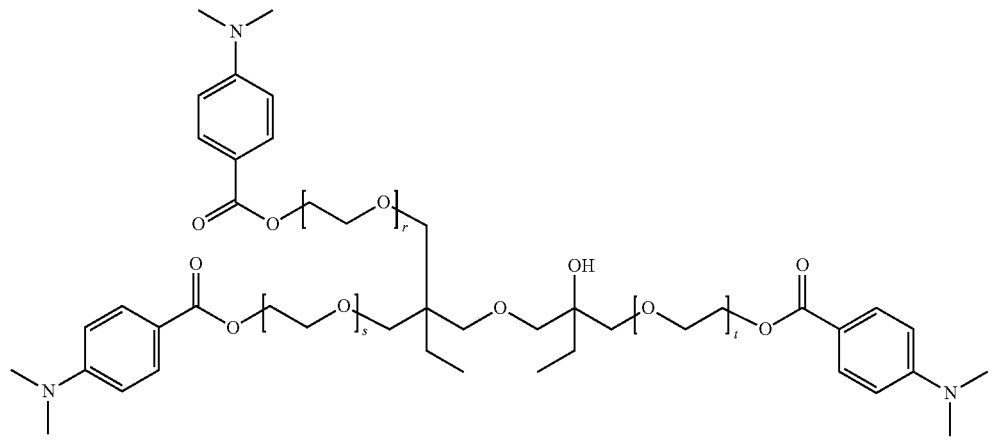

Formula II wherein r, s and t independently represent integers from 0 to 20.

In one embodiment, the compound of formula II may have r, s and t that are all equal to 0.

In another embodiment, the compound of formula II may be an ethoxylated compound. Accordingly, the compound of formula II may have at least one of r, s and t that is not equal to 0. In particular, the sum of r+s+t may be from 1 to 30, from 4 to 25, or from 6 to 20. More particularly, r, s and t may independently represent integers from 0 to 20, from 1 to 10 or from 2 to 5.

The ancillary amine may comprise a compound of formula II as defined above.

In another particularly preferred example, the compound according to Formula I is present in a mixture with the ancillary amine co-initiator according to Formula III.

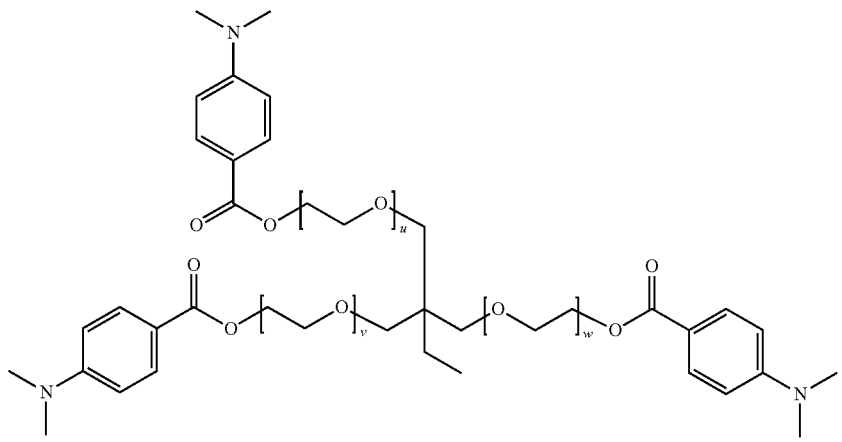

Formula III wherein u, v and w independently represent integers from 0 to 20.

In one embodiment, the compound of formula III may have u, v and w that are all equal to 0.

In another embodiment, the compound of formula III may be an ethoxylated compound. Accordingly, the compound of formula III may have at least one of u, v and w that is not equal to 0. In particular, the sum of u+v+w may be from 1 to 30, from 4 to 25, or from 6 to 20. More particularly, u, v and w may independently represent integers from 0 to 20, from 1 to 10 or from 2 to 5.

The ancillary amine may comprise a compound of formula III as defined above.

The ancillary amine may comprise a compound of formula IV

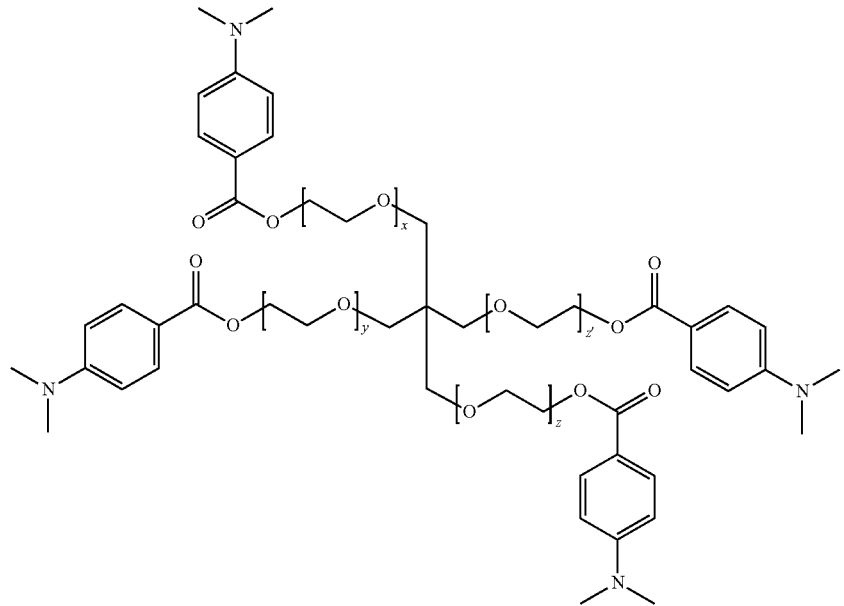

Formula IV wherein x, y, z and z' independently represent integers from 0 to 20.

In one embodiment, the compound of formula IV may have x, y, z and z' that are all equal to 0.

In another embodiment, the compound of formula IV may be an ethoxylated compound. Accordingly, the compound of formula IV may have at least one of x, y, z and z' that is not equal to 0. In particular, the sum of x+y+z+z' may be from 1 to 30, from 4 to 25, or from 6 to 20. More particularly, x, y, z and z' may independently represent integers from 0 to 20, from 1 to 10 or from 2 to 5.

The ancillary amine may comprise a compound of formula V

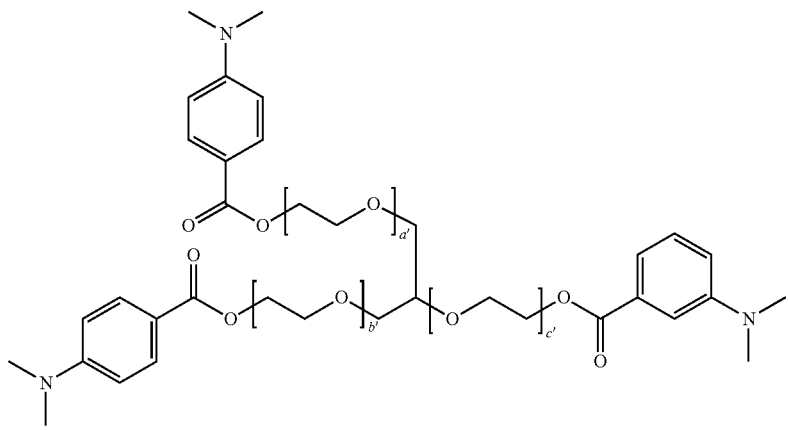

Formula V wherein a', b' and c' independently represent integers from 0 to 20.

In one embodiment, the compound of formula V may have a', b' and c' that are all equal to 0.

In another embodiment, the compound of formula V may be an ethoxylated compound. Accordingly, the compound of formula V may have at least one of a', b' and c' that is not equal to 0. In particular, the sum of a'+b'+c' may be from 1 to 30, from 4 to 25, or from 6 to 20. More particularly, a', b' and c' may independently represent integers from 0 to 20, from 1 to 10 or from 2 to 5.

The co-initiator is present as a mixture of a compound of Formula I and with one or more ancillary amines. The percentage of the compound according to Formula I in said mixture may be in the range of 0.1 to 99.9 wt %, preferably in the range of 5 to 95 wt %, more preferably in the range of 70 to 90 wt %, based on the weight of the co-initiator mixture. In these ranges, the co-initiator (i.e. the mixture of the compound of Formula I and the ancillary amine), can be formulated to offer a balance between reactivity and solubility. The remainder of this mixture will be composed of the ancillary amine.

The co-initiator mixture may comprise from 0.1 to 99.9%, from 5 to 95%, from 10 to 90%, from 15 to 85%, from 20 to 80%, from 25 to 75%, from 30 to 70%, from 35 to 65%, from 40 to 60%, or from 45 to 55%, by weight of the compound of formula I based on the weight of the co-initiator mixture. The amount of ancillary amine in the co-initiator mixture may represent the complement to 100% of the weight co-initiator mixture. In particular, the co-initiator mixture may comprise from 0.1 to 99.9%, from 5 to 95%, from 10 to 90%, from 15 to 85%, from 20 to 80%, from 25 to 75%, from 30 to 70%, from 35 to 65%, from 40 to 60%, or from 45 to 55%, by weight of ancillary amine based on the weight of the co-initiator mixture.

Alternatively, the co-initiator mixture may comprise from 0.1 to 99.9%, from 5 to 95%, from 10 to 90%, from 20 to 90%, from 30 to 90%, from 40 to 90%, from 50 to 90%, from 60 to 90%, from 70 to 90%, or from 80 to 90%, by weight of the compound of formula I based on the weight of the co-initiator mixture. The amount of ancillary amine in the co-initiator mixture may represent the complement to 100% of the weight co-initiator mixture. In particular, the co-initiator mixture may comprise from 0.1 to 99.9%, from 5 to 95%, from 10 to 90%, from 10 to 80%, from 10 to 70%, from 10 to 60%, from 10 to 50%, from 10 to 40%, from 10 to 30%, or from 10 to 20%, by weight of ancillary amine based on the weight of the co-initiator mixture.

Alternatively, the co-initiator mixture may comprise from 0.1 to 99.9%, from 5 to 95%, from 10 to 90%, from 10 to 80%, from 10 to 70%, from 10 to 60%, from 10 to 50%, from 10 to 40%, from 10 to 30%, or from 10 to 20%, by weight of the compound of formula I based on the weight of the co-initiator mixture. The amount of ancillary amine in the co-initiator mixture may represent the complement to 100% of the weight co-initiator mixture. In particular, the co-initiator mixture may comprise from 0.1 to 99.9%, from 5 to 95%, from 10 to 90%, from 20 to 90%, from 30 to 90%, from 40 to 90%, from 50 to 90%, from 60 to 90%, from 70 to 90%, or from 80 to 90%, by weight of ancillary amine based on the weight of the co-initiator mixture.

The compound of Formula I preferably has a molecular weight of greater than 500 Daltons, more preferably greater than 800 Daltons (often in the range 500-1500 Daltons, or in the range 800-1200 Daltons) to ensure controlled migration of the molecules. It is possible that the ancillary amine has a molecular weight similar to the compound of Formula I, to improve compatibility within the co-initiator, for instance by providing compounds of similar viscosity. Therefore, the ancillary amine may also have a molecular weight of greater than 500 Daltons, more preferably greater than 800 Daltons (often in the range 500-1500 Daltons, or in the range 800-1200 Daltons).

Some non-limiting examples of ancillary amines which might be included in the co-initiator mixture along with the compound according to Formula I are given in Table 1.

TABLE 1

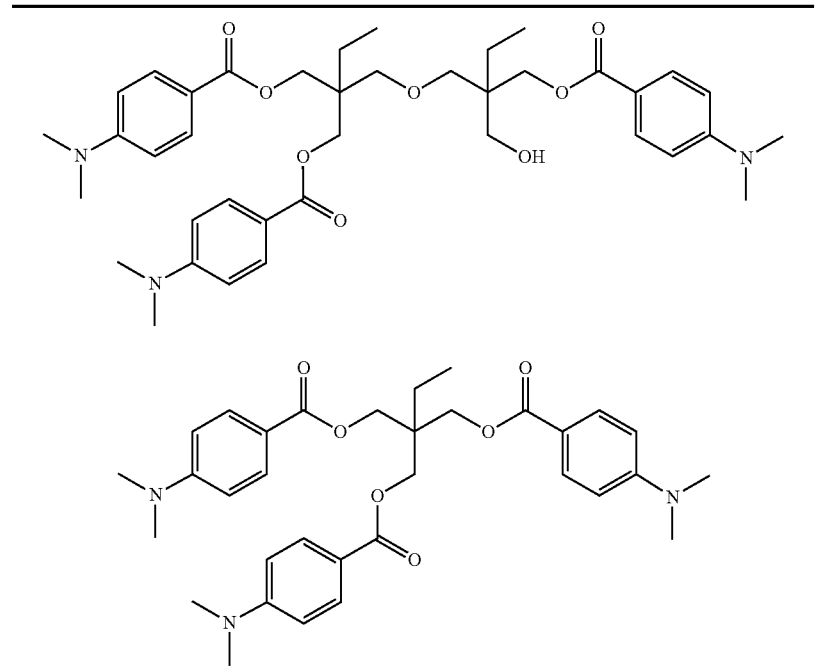

TABLE 1-continued
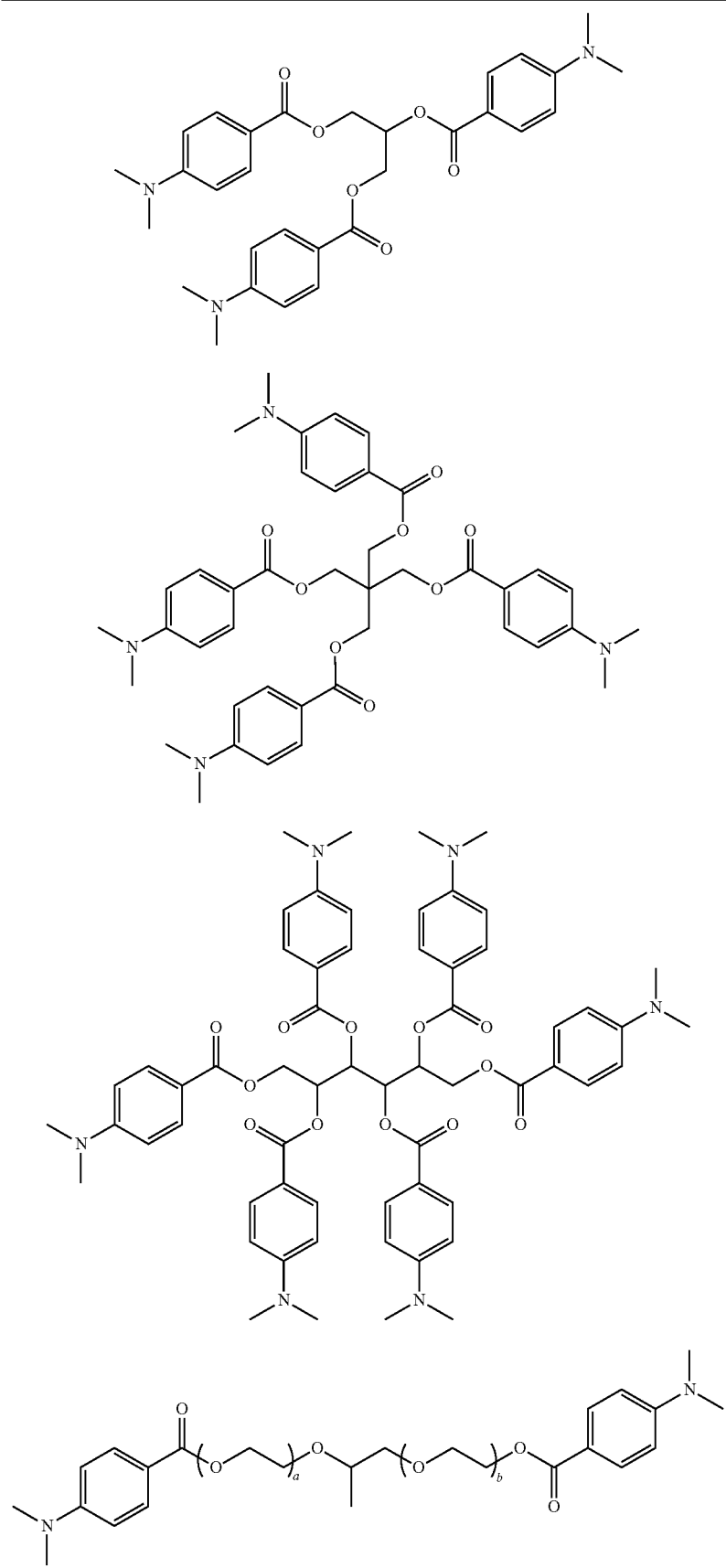

TABLE 1-continued

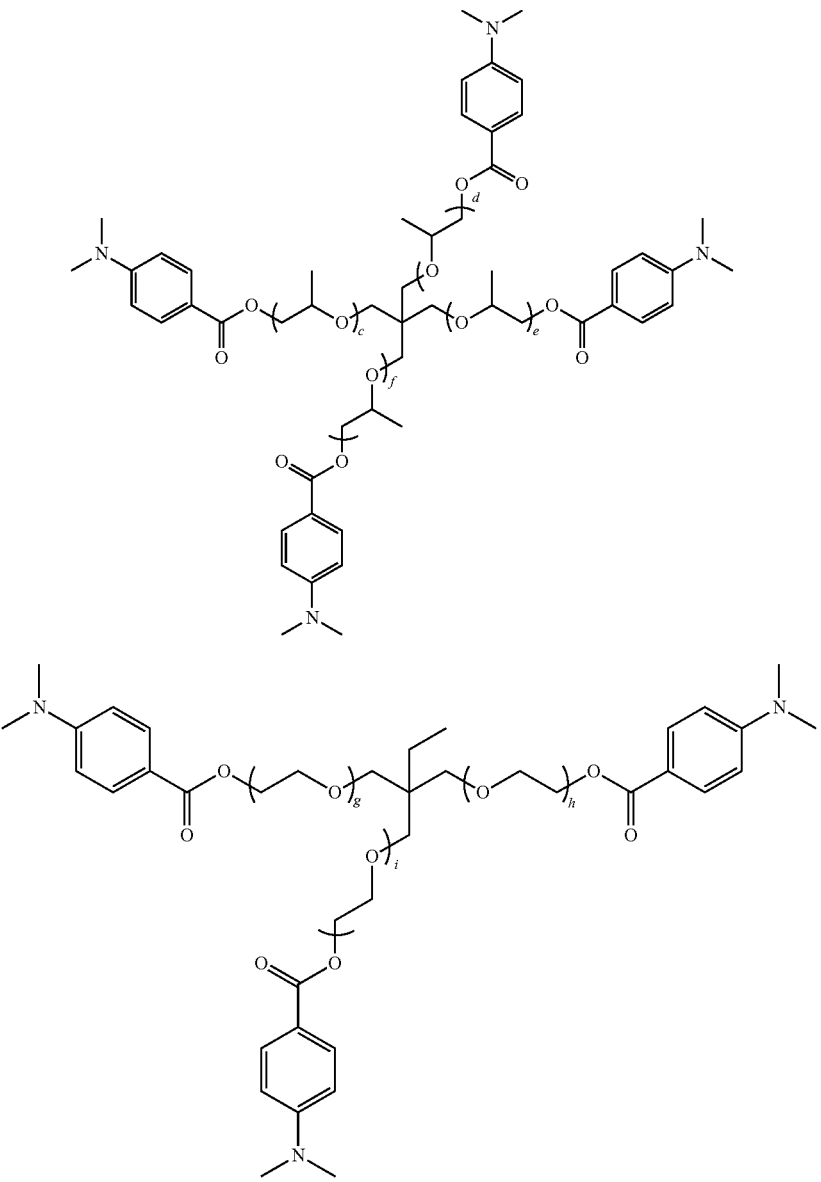

wherein a-i independently represent integers from 0-20, often 1-10 or 2-5.

In a second aspect of the invention, the co-initiator mixture including the compound according to Formula I is combined with one or more Type-I or Type-II photoinitiators, giving a photoinitiator blend. Preferably a Type-I photoinitiator is present in the photoinitiator blend. Type-I photoinitiators are more likely to form stable mixtures with amine co-initiators with minimal cross-reaction. Further, mixtures of Type-I photoinitiators with amine co-initiators may form liquid blends. Liquid blends are often more conveniently handled than solid mixtures. The photoinitiator may be present in solid or liquid form as appropriate for ease of formulation.

The Type-I or Type-II photoinitiator may be selected from benzoins, benzoin ethers, acetophenones, α-hydroxy acetophenones, aminoacetophenones, benzyl, benzyl ketals, anthraquinones, phosphine oxides, acylphosphine oxides, α-hydroxyketones, phenylglyoxylates, α-aminoketones, benzophenones, thioxanthones, xanthones, acridine derivatives, phenazene derivatives, quinoxaline derivatives, triazine compounds, benzoyl formates, aromatic oximes, metallocenes, acylsilyl or acylgermanyl compounds, camphorquinones, polymeric derivatives thereof, and mixtures thereof.

In one embodiment, the photoinitiator blend comprises a Type-II photoinitiator, in particular selected from diaryl ketones such as benzophenone (e.g. SpeedCure BP—Lambson Limited) or 4-benzoyl-4'-methyldiphenyl sulphide (e.g. SpeedCure BMS—Lambson Limited), thioxanthones such as 2-isopropylthioxanthone (e.g. SpeedCure 2-ITX—Lambson Limited), and combinations of thereof. Diffusion-hindered photoinitiators, in particular polymeric benzophenones or thioxanthones such as SpeedCure 7010 (Lambson Limited) or SpeedCure 7005 (Lambson Limited), may alternatively be used for certain low migration applications.

In one embodiment, the photoinitiator blend comprises a Type-I photoinitiator, in particular selected from an acetophenone, an α-hydroxy acetophenone such as 2-hydroxy-2-methyl-1-phenylpropanone (e.g. SpeedCure 73—Lambson Limited), an aminoacetophenone, a phosphine oxide and mixtures thereof. SpeedCure 73 may advantageously form liquid formulations with the co-initiators of the invention, providing handling benefits.

The co-initiator mixture as defined in the first aspect of the invention may be present in the photoinitiator blend in a total concentration in the range of 1 to 99 wt %, more preferably in a concentration in the range of 10 to 90 wt %, most preferably in a concentration in the range of 40 to 70 wt %, of the total weight of the photoinitiator blend. These ranges provide adequate balance between reactivity and viscosity.

In a third aspect of the invention there is provided a radiation-curable composition comprising the co-initiator mixture of the first aspect of the invention, one or more photoinitiators and one or more polymerisable monomers, oligomers or prepolymers. Typically, the photoinitiators will be Type-I or Type-II photoinitiators as described above.

The radiation-curable composition preferably comprises the co-initiator mixture as defined in the first aspect of the invention in a concentration in the range of 0.1 to 50 wt %, more preferably in a concentration in the range of 0.5 to 25 wt %, most preferably in a concentration in the range of 1 to 10 wt % of the total weight of the radiation-curable composition. The photoinitiators are typically present in the range of 1 to 5 wt % of the total weight of the radiation-curable composition.

Examples of photoinitiators which might be used in the radiation-curable composition in conjunction with the co-initiator mixture as defined by this invention include diaryl ketones such as benzophenone (e.g. SpeedCure BP—Lambson Limited) or 4-benzoyl-4'-methyldiphenyl sulphide (e.g. SpeedCure BMS—Lambson Limited), or thioxanthones such as 2-isopropylthioxanthone (e.g. SpeedCure 2-ITX—Lambson Limited), or combinations of these, without being limited thereto. Diffusion-hindered photoinitiators, such as SpeedCure 7010 (Lambson Limited) or SpeedCure 7005 (Lambson Limited), may alternatively be used for certain low migration applications.

The polymerisable monomers, oligomers or prepolymers which may be employed in the radiation-curable composition along with the co-initiator can include any polymerisable compound known in the art, but are preferably monofunctional or multifunctional acrylate or methacrylate-containing compounds as these structures provide good reactivity. Examples would include neopentyl glycol diacrylate, trimethylolpropane triacrylate, di(trimethylolpropane) tetraacrylate, dipentaerythritol pentaacrylate, hydroxyethyl methacrylate or bisphenol A dimethacrylate, and ethoxylated or propoxylated variants thereof, without being limited thereto.

In one embodiment, the radiation-curable composition of the invention comprise a (meth)acrylate-functionalized compound. The radiation-curable composition may comprise a mixture of (meth)acrylate-functionalized compounds. A (meth)acrylate-functionalized compound may be described as an organic compound bearing one or more (meth)acrylate functional groups per molecule. (Meth)acrylate-functionalized compounds are capable of participating in a free radical reaction or anionic reaction, in particular a reaction initiated by ultraviolet radiation or electron beam radiation. Such reactions may result in a polymerization or curing whereby the (meth)acrylate-functionalized compound becomes part of a polymerized matrix or polymeric chain. In various embodiments of the invention, the (meth)acrylate-functionalized compound may contain one, two, three, four, five or more (meth)acrylate functional groups per molecule. Combinations of multiple (meth)acrylate-functionalized compounds containing different numbers of (meth)acrylate groups may be utilized in the radiation-curable compositions of the present invention.

The radiation-curable compositions of the present invention may thus contain one or more (meth)acrylate functional compounds capable of undergoing free radical and/or anionic polymerization (curing) initiated by exposure to ultraviolet or electron beam radiation. The (meth)acrylate-functionalized compounds may be oligomers or monomers or a combination of oligomer(s) and monomer(s).

In one embodiment, the radiation-curable composition may comprise one or more (meth)acrylate-functionalized monomers, one or more (meth)acrylate-functionalized oligomers and mixtures thereof.

As used herein, the term "(meth)acrylate-functionalized monomer" means a monomer comprising a (meth)acrylate group, in particular an acrylate group. The term "(meth)acrylate-functionalized oligomer" means an oligomer comprising a (meth)acrylate group, in particular an acrylate group.

Any of the following types of (meth)acrylate-functionalized compounds may, for example, be employed in the radiation-curable compositions of the present invention: monomers such as (meth)acrylate esters of aliphatic mono-alcohols, (meth)acrylate esters of alkoxylated aliphatic mono-alcohols, (meth)acrylate esters of aliphatic polyols, (meth)acrylate esters of alkoxylated aliphatic polyols, (meth)acrylate esters of aromatic ring-containing alcohols, and (meth)acrylate esters of alkoxylated aromatic ring-containing alcohols; and oligomers such as epoxy (meth)acrylates, polyether (meth)acrylates, urethane (meth)acrylates, polyester (meth)acrylates, the amine- and sulfide-modified derivatives thereof; and combinations thereof.

In one embodiment, the radiation-curable composition comprises a (meth)acrylate-functionalized monomer. The radiation-curable composition may comprise a mixture of (meth)acrylate-functionalized monomers.

The (meth)acrylate-functionalized monomer may have a molecular weight of less than 600 g/mol, in particular from 100 to 550 g/mol, more particularly 200 to 500 g/mol.

The (meth)acrylate-functionalized monomer may have 1 to 6 (meth)acrylate groups, in particular 1 to 3 (meth)acrylate groups, more particularly 1 to 3 acrylate groups.

The (meth)acrylate-functionalized monomer may comprise a mixture of (meth)acrylate-functionalized monomers having different functionalities. For example the (meth)acrylate-functionalized monomer may comprise a mixture of a (meth)acrylate-functionalized monomer containing a single acrylate or methacrylate group per molecule (referred to herein as "mono(meth)acrylate-functionalized compounds") and a (meth)acrylate-functionalized monomer containing 2 or more, preferably 2 or 3, acrylate and/or methacrylate groups per molecule.

In one embodiment, the (meth)acrylate functionalized monomer comprises a mono(meth)acrylate-functionalized monomer. The mono(meth)acrylate-functionalized monomer may advantageously function as a reactive diluent and reduce the viscosity of the composition of the invention. Examples of suitable mono(meth)acrylate-functionalized monomers include, but are not limited to, mono-(meth)acrylate esters of aliphatic alcohols (wherein the aliphatic alcohol may be straight chain, branched or alicyclic and may be a mono-alcohol, a di-alcohol or a polyalcohol, provided only one hydroxyl group is esterified with (meth)acrylic acid); mono-(meth)acrylate esters of aromatic alcohols (such as phenols, including alkylated phenols); mono-(meth) acrylate esters of alkylaryl alcohols (such as benzyl alcohol); mono-(meth)acrylate esters of oligomeric and polymeric glycols such as diethylene glycol, triethylene glycol, dipropylene glycol, tripropylene glycol, polyethylene glycol, and polypropylene glycol); mono-(meth)acrylate esters of monoalkyl ethers of glycols and oligoglycols; mono-(meth) acrylate esters of alkoxylated (e.g., ethoxylated and/or propoxylated) aliphatic alcohols (wherein the aliphatic alcohol may be straight chain, branched or alicyclic and may be a mono-alcohol, a di-alcohol or a polyalcohol, provided only one hydroxyl group of the alkoxylated aliphatic alcohol is esterified with (meth)acrylic acid); mono-(meth)acrylate esters of alkoxylated (e.g., ethoxylated and/or propoxylated) aromatic alcohols (such as alkoxylated phenols); caprolactone mono(meth)acrylates; and the like.

The following compounds are specific examples of mono (meth)acrylate-functionalized monomers suitable for use in the radiation-curable compositions of the present invention: methyl (meth)acrylate; ethyl (meth)acrylate; n-propyl (meth)acrylate; n-butyl (meth)acrylate; isobutyl (meth)acrylate; n-hexyl (meth)acrylate; 2-ethylhexyl (meth)acrylate; n-octyl (meth)acrylate; isooctyl (meth)acrylate; n-decyl (meth)acrylate; n-dodecyl (meth)acrylate; tridecyl (meth) acrylate; tetradecyl (meth)acrylate; hexadecyl (meth)acrylate; 2-hydroxyethyl (meth)acrylate; 2- and 3-hydroxypropyl (meth)acrylate; 2-methoxyethyl (meth)acrylate; 2-ethoxyethyl (meth)acrylate; 2- and 3-ethoxypropyl (meth) acrylate; tetrahydrofurfuryl (meth)acrylate; alkoxylated tetrahydrofurfuryl (meth)acrylate; 2-(2-ethoxyethoxy)ethyl (meth)acrylate; cyclohexyl (meth)acrylate; glycidyl (meth) acrylate; isodecyl (meth)acrylate: 2-phenoxyethyl (meth) acrylate; lauryl (meth)acrylate; alkoxylated phenol (meth) acrylates; alkoxylated nonylphenol (meth)acrylates; cyclic trimethylolpropane formal (meth)acrylate; isobornyl (meth) acrylate; tricyclodecanemethanol (meth)acrylate; tert-butylcyclohexanol (meth)acrylate; trimethylcyclohexanol (meth) acrylate; diethylene glycol monomethyl ether (meth) acrylate; diethylene glycol monoethyl ether (meth)acrylate; diethylene glycol monobutyl ether (meth)acrylate; triethylene glycol monoethyl ether (meth)acrylate; ethoxylated lauryl (meth)acrylate; methoxy polyethylene glycol (meth) acrylates; hydroxyl ethyl-butyl urethane (meth)acrylates; 3-(2-hydroxyalkyl)oxazolidinone (meth)acrylates; and combinations thereof.

In one embodiment, the (meth)acrylate functionalized monomer may comprise a (meth)acrylate-functionalized monomer containing two or more (meth)acrylate groups per molecule. Examples of suitable (meth)acrylate-functionalized monomers containing two or more (meth)acrylate groups per molecule include acrylate and methacrylate esters of polyhydric alcohols (organic compounds containing two or more, e.g., 2 to 6, hydroxyl groups per molecule). Specific examples of suitable polyhydric alcohols include $C_{2-20}$ alkylene glycols (glycols having a $C_{2-10}$ alkylene group may be preferred, in which the carbon chain may be branched; e.g., ethylene glycol, trimethylene glycol, 1,2-propylene glycol, 1,2-butanediol, 1,3-butanediol, 2,3-butanediol, tetramethylene glycol (1,4-butanediol), 1,5-pentanediol, 1,6-hexanediol, 1,8-octanediol, 1,9-nonanediol, 1,12-dodecanediol, cyclohexane-1,4-dimethanol, bisphenols, and hydrogenated bisphenols, as well as alkoxylated (e.g., ethoxylated and/or propoxylated) derivatives thereof), diethylene glycol, glycerin, alkoxylated glycerin, triethylene glycol, dipropylene glycol, tripropylene glycol, trimethylolpropane, alkoxylated trimethylolpropane, ditrimethylolpropane, alkoxylated ditrimethylolpropane, pentaerythritol, alkoxylated pentaerythritol, dipentaerythritol, alkoxylated dipentaerythritol, cyclohexanediol, alkoxylated cyclohexanediol, cyclohexanedimethanol, alkoxylated cyclohexanedimethanol, norbornene dimethanol, alkoxylated norbornene dimethanol, norbornane dimethanol, alkoxylated norbornane dimethanol, polyols containing an aromatic ring, cyclohexane-1,4-dimethanol ethylene oxide adducts, bisphenol ethylene oxide adducts, hydrogenated bisphenol ethylene oxide adducts, bisphenol propylene oxide adducts, hydrogenated bisphenol propylene oxide adducts, cyclohexane-1,4-dimethanol propylene oxide adducts, sugar alcohols and alkoxylated sugar alcohols. Such polyhydric alcohols may be fully or partially esterified (with (meth)acrylic acid, (meth)acrylic anhydride, (meth)acryloyl chloride or the like), provided they contain at least two (meth)acrylate functional groups per molecule. As used herein, the term "alkoxylated" refers to compounds containing one or more oxyalkylene moieties (e.g., oxyethylene and/or oxypropylene moieties). An oxyalkylene moiety corresponds to the general structure —R—O—, wherein R is a divalent aliphatic moiety such as —$CH_2CH_2$— or —$CH_2CH(CH_3)$—. For example, an alkoxylated compound may contain from 1 to 30 oxyalkylene moieties per molecule.

Exemplary (meth)acrylate-functionalized monomers containing two or more (meth)acrylate groups per molecule may include ethoxylated bisphenol A di(meth)acrylates; triethylene glycol di(meth)acrylate; ethylene glycol di(meth)acrylate; tetraethylene glycol di(meth)acrylate; polyethylene glycol di(meth)acrylates; 1,4-butanediol diacrylate; 1,4-butanediol dimethacrylate; diethylene glycol diacrylate; diethylene glycol dimethacrylate, 1,6-hexanediol diacrylate; 1,6-hexanediol dimethacrylate; neopentyl glycol diacrylate; neopentyl glycol di(meth)acrylate; polyethylene glycol (600) dimethacrylate (where 600 refers to the approximate number average molecular weight of the polyethylene glycol portion); polyethylene glycol (200) diacrylate; 1,12-dodecanediol dimethacrylate; tetraethylene glycol diacrylate; triethylene glycol diacrylate, 1,3-butylene glycol dimethacrylate, tripropylene glycol diacrylate, polybutadiene diacrylate; methyl pentanediol diacrylate; polyethylene glycol (400) diacrylate; ethoxylated$_2$ bisphenol A dimethacrylate; ethoxylated$_3$ bisphenol A dimethacrylate; ethoxylated$_3$ bisphenol A diacrylate; cyclohexane dimethanol dimethacrylate; cyclohexane dimethanol diacrylate; ethoxylated$_{10}$ bisphenol A dimethacrylate (where the numeral following "ethoxylated" is the average number of oxyalkylene moieties per molecule); dipropylene glycol diacrylate; ethoxylated$_4$ bisphenol A dimethacrylate; ethoxylated$_6$ bisphenol A dimethacrylate; ethoxylated$_8$ bisphenol A dimethacrylate; alkoxylated hexanediol diacrylates; alkoxylated cyclohexane dimethanol diacrylate; dodecane diacrylate; ethoxylated$_4$ bisphenol A diacrylate; ethoxylated$_{10}$ bisphenol A diacrylate; polyethylene glycol (400) dimethacrylate; polypropylene glycol (400) dimethacrylate; metallic diacrylates; modified metallic diacrylates; metallic dimethacrylates; polyethylene glycol (1000) dimethacrylate; methacrylated polybutadiene; propoxylated$_2$ neopentyl glycol diacrylate; ethoxylated$_{30}$ bisphenol A dimethacrylate; ethoxylated$_{30}$ bisphenol A diacrylate; alkoxylated neopentyl glycol diacrylates; polyethylene glycol dimethacrylates; 1,3-butylene glycol diacrylate; ethoxylated$_2$ bisphenol A dimethacrylate; dipropylene glycol diacrylate; ethoxylated$_4$ bisphenol A diacrylate; polyethylene glycol (600) diacrylate; polyethylene glycol (1000) dimethacrylate; tricyclodecane dimethanol diacrylate; propoxylated neopentyl glycol diacrylates such as propoxylated$_2$ neopentyl glycol diacrylate; diacrylates of alkoxylated aliphatic alcohols; trimethylolpropane trimethacrylate; trimethylolpropane triacrylate; tris (2-hydroxyethyl) isocyanurate triacrylate; ethoxylated$_{20}$ trimethylolpropane triacrylate; pentaerythritol triacrylate; ethoxylated$_3$ trimethylolpropane triacrylate; propoxylated$_3$ trimethylolpropane triacrylate; ethoxylated$_6$ trimethylolpropane triacrylate; propoxylated$_6$ trimethylolpropane triacrylate; ethoxylated$_9$ trimethylolpropane triacrylate; alkoxylated trifunctional acrylate esters; trifunctional methacrylate esters; trifunctional acrylate esters; propoxylated$_3$ glyceryl triacrylate; propoxylated$_{5.5}$ glyceryl triacrylate; ethoxylated$_{15}$ trimethylolpropane triacrylate; trifunctional phosphoric acid esters; trifunctional acrylic acid esters; pentaerythritol tetraacrylate; di-trimethylolpropane tetraacrylate; ethoxylated$_4$ pentaerythritol tetraacrylate; pentaerythritol polyoxyethylene tetraacrylate; dipentaerythritol pentaacrylate; and pentaacrylate esters.

The radiation-curable composition of the invention may comprise 10 to 80%, in particular 15 to 75%, more particularly 20 to 70%, by weight of (meth)acrylate-functionalized monomer based on the total weight of the radiation-curable composition.

In one embodiment, the radiation-curable composition comprises a (meth)acrylate-functionalized oligomer. The radiation-curable composition may comprise a mixture of (meth)acrylate-functionalized oligomers.

The (meth)acrylate-functionalized oligomer may be selected in order to enhance the flexibility, strength and/or modulus, among other attributes, of a cured polymer prepared using the radiation-curable composition of the present invention.

The (meth)acrylate functionalized oligomer may have 1 to 18 (meth)acrylate groups, in particular 2 to 6 (meth)acrylate groups, more particularly 2 to 6 acrylate groups.

The (meth)acrylate functionalized oligomer may have a number average molecular weight equal or more than 600 g/mol, in particular 800 to 15,000 g/mol, more particularly 1,000 to 5,000 g/mol.

In particular, the (meth)acrylate-functionalized oligomers may be selected from the group consisting of (meth)acrylate-functionalized urethane oligomers (sometimes also referred to as "urethane (meth)acrylate oligomers," "polyurethane (meth)acrylate oligomers" or "carbamate (meth)acrylate oligomers"), (meth)acrylate-functionalized epoxy oligomers (sometimes also referred to as "epoxy (meth)acrylate oligomers"), (meth)acrylate-functionalized polyether oligomers (sometimes also referred to as "polyether (meth)acrylate oligomers"), (meth)acrylate-functionalized polydiene oligomers (sometimes also referred to as "polydiene (meth)acrylate oligomers"), (meth)acrylate-functionalized polycarbonate oligomers (sometimes also referred to as "polycarbonate (meth)acrylate oligomers"), and (meth)acrylate-functionalized polyester oligomers (sometimes also referred to as "polyester (meth)acrylate oligomers") and mixtures thereof.

Preferably, the (meth)acrylate-functionalized oligomer comprises a (meth)acrylate-functionalized urethane oligomer, more preferably an acrylate-functionalized urethane oligomer. Advantageously, the (meth)acrylate-functionalized oligomer comprises a (meth)acrylate-functionalized urethane oligomer having two (meth)acrylate groups, more preferably an acrylate-functionalized urethane oligomer having two acrylate groups.

Exemplary polyester (meth)acrylate oligomers include the reaction products of acrylic or methacrylic acid or mixtures or synthetic equivalents thereof with hydroxyl group-terminated polyester polyols. The reaction process may be conducted such that all or essentially all of the hydroxyl groups of the polyester polyol have been (meth)acrylated, particularly in cases where the polyester polyol is difunctional. The polyester polyols can be made by polycondensation reactions of polyhydroxyl functional components (in particular, diols) and polycarboxylic acid functional compounds (in particular, dicarboxylic acids and anhydrides). The polyhydroxyl functional and polycarboxylic acid functional components can each have linear, branched, cycloaliphatic or aromatic structures and can be used individually or as mixtures.

Examples of suitable epoxy (meth)acrylates include the reaction products of acrylic or methacrylic acid or mixtures thereof with an epoxy resin (polyglycidyl ether or ester). The epoxy resin may, in particular, by selected from bisphenol A diglycidyl ether, bisphenol F diglycidyl ether, bisphenol S diglycidyl ether, brominated bisphenol A diglycidyl ether, brominated bisphenol F diglycidyl ether, brominated bisphenol S diglycidyl ether, epoxy novolak resin, hydrogenated bisphenol A diglycidyl ether, hydrogenated bisphenol F diglycidyl ether, hydrogenated bisphenol S diglycidyl ether, 3,4-epoxycyclohexylmethyl-3',4'-epoxycyclohexanecarboxylate, 2-(3,4-epoxycyclohexyl-5,5-spiro-3,4-epoxy) cyclohexane-1,4-dioxane, bis(3,4-epoxycyclohexylmethyl) adipate, vinylcyclohexene oxide, 4-vinylepoxycyclohexane, bis(3,4-epoxy-6-methylcyclohexylmethyl)adipate, 3,4-epoxy-6-methylcyclohexyl-3',4'-epoxy-6'-methylcyclohexanecarboxylate, methylenebis(3,4-epoxycyclohexane), dicyclopentadiene diepoxide, di(3,4-epoxycyclohexylmethyl) ether of ethylene glycol, ethylenebis(3,4-epoxycyclohexanecarboxylate), 1,4-butanediol diglycidyl ether, 1,6-hexanediol diglycidyl ether, glycerol triglycidyl ether, trimethylolpropane triglycidyl ether, polyethylene glycol diglycidyl ether, polypropylene glycol diglycidyl ether, polyglycidyl ethers of a polyether polyol obtained by the addition of one or more alkylene oxides to an aliphatic polyhydric alcohol such as ethylene glycol, propylene glycol, and glycerol, diglycidyl esters of aliphatic long-chain dibasic acids, monoglycidyl ethers of aliphatic higher alcohols, monoglycidyl ethers of phenol, cresol, butyl phenol, or polyether alcohols obtained by the addition of alkylene oxide to these compounds, glycidyl esters of higher fatty acids, epoxidized soybean oil, epoxybutylstearic acid, epoxyoctylstearic acid, epoxidized linseed oil, epoxidized polybutadiene, and the like.

Suitable polyether (meth)acrylate oligomers include, but are not limited to, the condensation reaction products of acrylic or methacrylic acid or synthetic equivalents or mixtures thereof with polyetherols which are polyether polyols (such as polyethylene glycol, polypropylene glycol or polytetramethylene glycol). Suitable polyetherols can be linear or branched substances containing ether bonds and terminal hydroxyl groups. Polyetherols can be prepared by ring opening polymerization of cyclic ethers such as tetrahydrofuran or alkylene oxides (e.g., ethylene oxide and/or propylene oxide) with a starter molecule. Suitable starter molecules include water, polyhydroxyl functional materials, polyester polyols and amines.

Polyurethane (meth)acrylate oligomers (sometimes also referred to as "urethane (meth)acrylate oligomers") suitable for use in the radiation-curable compositions of the present invention include urethanes based on aliphatic, cycloaliphatic and/or aromatic polyester polyols and polyether polyols and aliphatic, cycloaliphatic and/or aromatic polyester diisocyanates and polyether diisocyanates capped with (meth)acrylate end-groups. Suitable polyurethane (meth)

acrylate oligomers include, for example, aliphatic polyester-based urethane di- and tetra-acrylate oligomers, aliphatic polyether-based urethane di- and tetra-acrylate oligomers, as well as aliphatic polyester/polyether-based urethane di- and tetra-acrylate oligomers.

The polyurethane (meth)acrylate oligomers may be prepared by reacting aliphatic, cycloaliphatic and/or aromatic polyisocyanates (e.g., diisocyanate, triisocyanate) with OH group terminated polyester polyols, polyether polyols, polycarbonate polyols, polycaprolactone polyols, polyorganosiloxane polyols (e.g., polydimethylsiloxane polyols), or polydiene polyols (e.g., polybutadiene polyols), or combinations thereof to form isocyanate-functionalized oligomers which are then reacted with hydroxyl-functionalized (meth)acrylates such as hydroxyethyl acrylate or hydroxyethyl methacrylate to provide terminal (meth)acrylate groups. For example, the polyurethane (meth)acrylate oligomers may contain two, three, four or more (meth)acrylate functional groups per molecule. Other orders of addition may also be practiced to prepare the polyurethane (meth)acrylate, as is known in the art. For example, the hydroxyl-functionalized (meth)acrylate may be first reacted with a polyisocyanate to obtain an isocyanate-functionalized (meth)acrylate, which may then be reacted with an OH group terminated polyester polyol, polyether polyol, polycarbonate polyol, polycaprolactone polyol, polydimethysiloxane polyol, polybutadiene polyol, or a combination thereof. In yet another embodiment, a polyisocyanate may be first reacted with a polyol, including any of the aforementioned types of polyols, to obtain an isocyanate-functionalized polyol, which is thereafter reacted with a hydroxyl-functionalized (meth)acrylate to yield a polyurethane (meth)acrylate. Alternatively, all the components may be combined and reacted at the same time.

Suitable acrylic (meth)acrylate oligomers (sometimes also referred to in the art as "acrylic oligomers") include oligomers which may be described as substances having an oligomeric acrylic backbone which is functionalized with one or (meth)acrylate groups (which may be at a terminus of the oligomer or pendant to the acrylic backbone). The acrylic backbone may be a homopolymer, random copolymer or block copolymer comprised of repeating units of acrylic monomers. The acrylic monomers may be any monomeric (meth)acrylate such as C1-C6 alkyl (meth)acrylates as well as functionalized (meth)acrylates such as (meth)acrylates bearing hydroxyl, carboxylic acid and/or epoxy groups. Acrylic (meth)acrylate oligomers may be prepared using any procedures known in the art, such as by oligomerizing monomers, at least a portion of which are functionalized with hydroxyl, carboxylic acid and/or epoxy groups (e.g., hydroxyalkyl(meth)acrylates, (meth)acrylic acid, glycidyl (meth)acrylate) to obtain a functionalized oligomer intermediate, which is then reacted with one or more (meth)acrylate-containing reactants to introduce the desired (meth)acrylate functional groups.

Any of the above-mentioned types of oligomers may be modified with amines or sulfides (e.g., thiols), following procedures known in the art. Such amine- and sulfide-modified oligomers may be prepared, for example, by reacting a relatively small portion (e.g., 2-15%) of the (meth) acrylate functional groups present in the base oligomer with an amine (e.g., a secondary amine) or a sulfide (e.g., a thiol), wherein the modifying compound adds to the carbon-carbon double bond of the (meth)acrylate in a Michael addition reaction.

The radiation-curable composition of the invention may comprise 10 to 80%, in particular 15 to 75%, more particularly 20 to 70%, by weight of (meth)acrylate-functionalized oligomer based on the total weight of the radiation-curable composition.

The co-initiator mixture according to the present invention can be used in any radiation-curable composition including varnishes, lacquers or printing inks. Said compositions may additionally contain other additives such as dispersants, dispersion synergists, inhibitors, surfactants, or colourants, i.e. pigments or dyes.

The co-initiator including the compound according to Formula I can be prepared by a simple condensation reaction between a suitable acid chloride and two or more alcohols or polyols, including di(trimethyolpropane), providing a mixture of product esters in the same reaction vessel (Scheme 1). Said mixture can then be isolated and purified using acid-base extraction.

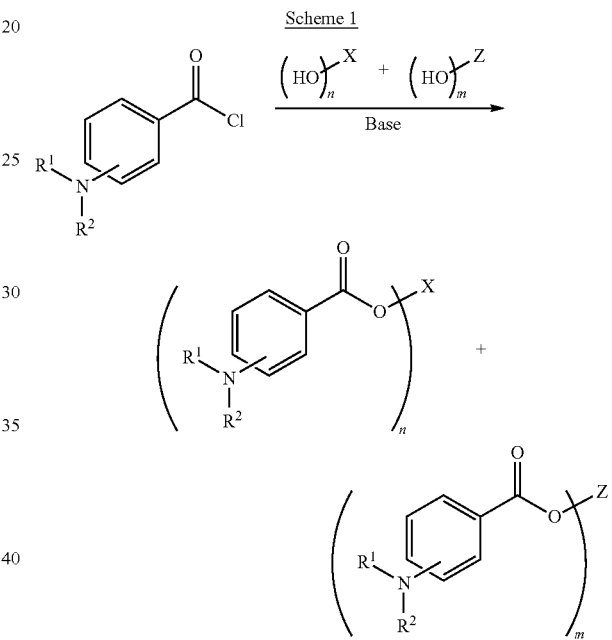

Scheme 1 wherein $R^1$ and $R^2$ independently represent methyl or ethyl groups and n and m represent integers. Often n and m will independently be integers in the range of 1 to 8, often in the range of 2 to 4, including 2, 3 and 4.

Use of only one polyol (specifically di(trimethyolpropane)) can also give a mixture of fully and partially-substituted products depending on the stoichiometry of the polyol and acid chloride used, also leading to a mixture of products (Scheme 2).

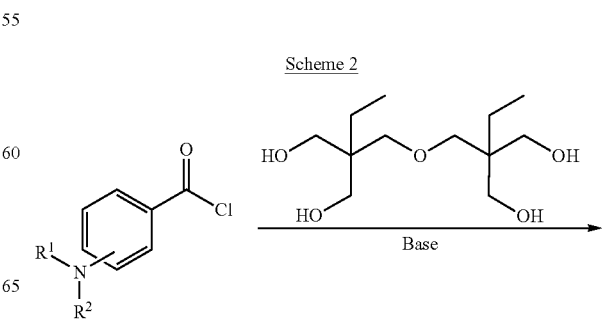

Scheme 2

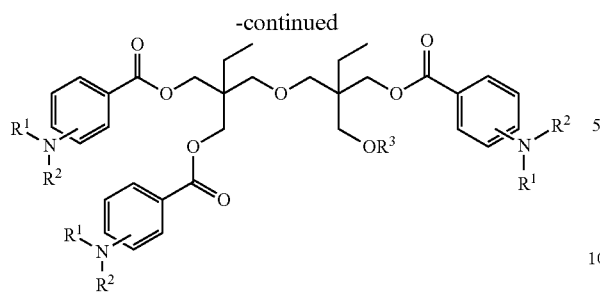

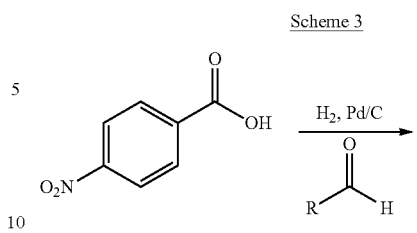

Scheme 3

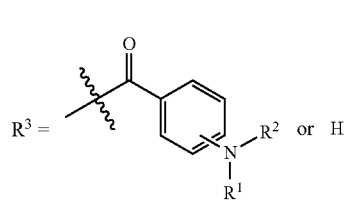

wherein R¹ and R² independently represent methyl or ethyl groups.

The corresponding ethoxylated compounds may be obtained in similar fashion using an ethoxylated polyol (specifically ethoxylated di(trimethyolpropane)).

Examples of suitable acid chlorides for making the co-initiator including the compound according to Formula I include 4-(dimethylamino)benzoyl chloride, 4-(diethylamino)benzoyl chloride and 4-[ethyl(methyl)amino]benzoyl chloride, or the hydrochloride salts thereof.

Examples of suitable polyols for making the co-initiator including the compound according to Formula I include di(trimethylolpropane), trimethylolpropane, glycerol, pentaerythritol, dipentaerythritol, tripentaerythritol, sorbitol, mannitol, glucose, sucrose, neopentyl glycol, any ethoxylated or propoxylated variants thereof, as well as any stereoisomeric forms therefore, without being limited thereto.

Alternatively, a co-initiator including the compound according to Formula I can be prepared by the synthesis of the compound of Formula I and the ancillary amine separately, for example by the reaction of alcohols with suitable acid chlorides, then the compound of Formula I and the ancillary amine can be combined in the desired proportions, for example by dissolving these compounds in a suitable solvent and then removing the solvent to provide the mixture.

N,N-Dimethylaminobenzoate esters can be prepared using the methods described above from N,N-dimethylaminobenzoic acid, which itself can be prepared via the reductive alkylation of nitrobenzoic acid in the presence of formaldehyde, a suitable reducing agent (e.g. hydrogen) and a suitable catalyst. An acid chloride can be prepared by reacting the carboxylic acid with a suitable chlorinating reagent such as thionyl chloride (Scheme 3).

To prepare N,N-diethylamino variants of these products, the necessary N,N-diethylaminobenzoic acid intermediate can be prepared via the reductive alkylation of nitrobenzoic acid in the presence of acetaldehyde, a reducing agent and a catalyst. Mixed methyl and ethyl substituted derivatives can be prepared via stepwise alkylation using both formaldehyde and acetaldehyde in turn.

wherein R represents H or a methyl group

Alternatively, a mixture of multifunctional nitrobenzoate esters may be prepared by the esterification of nitrobenzoic acid with one or more polyols, including di(trimethylolpropane), in the presence of an acid catalyst such as sulfuric acid or p-toluenesulfonic acid (Scheme 4). Reductive alkylation of this mixture of nitrobenzoate esters using formaldehyde or acetaldehyde in the presence of a suitable reducing agent and catalyst may likewise give a mixture of dialkylaminobenzoate esters including the compound according to Formula I (Scheme 5).

Scheme 4

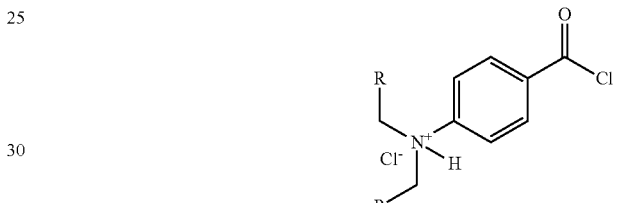

wherein n and m represent integers. Often n and m will independently be integers in the range of 1 to 8, often in the range of 2 to 4, including 2, 3 and 4.

Scheme 5

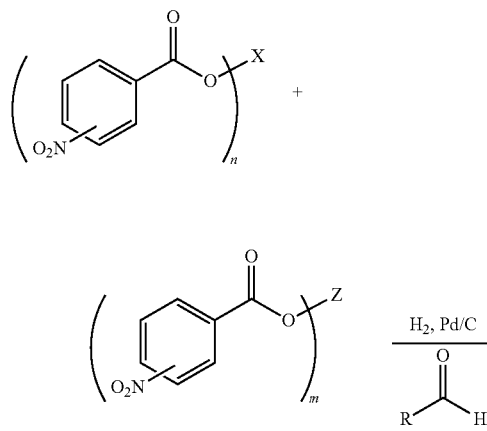

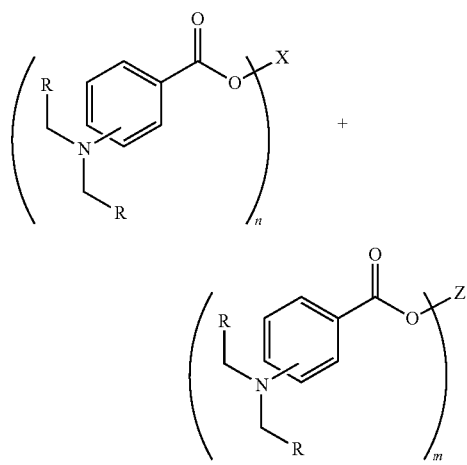

wherein R represents H or a methyl group and n and m represent integers. Often n and m will independently be integers in the range of 1 to 8, often in the range of 2 to 4, including 2, 3 and 4.

Dialkylaminobenzoate derivatives can also be prepared via nucleophilic aromatic substitution reactions between dialkylamines (such as dimethylamine or diethylamine) and fluorobenzoate derivatives in the presence of a suitable base (Scheme 6). Other halogen substituted aromatic esters such as chlorobenzoate or bromobenzoate esters, or compounds containing other leaving groups such as iodide or triflate, may also be used under more forcing conditions or if a cross-coupling catalyst such as a transition metal salt is employed.

Scheme 6

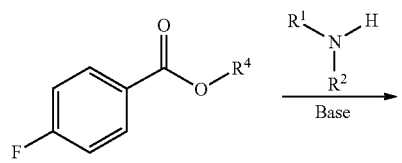

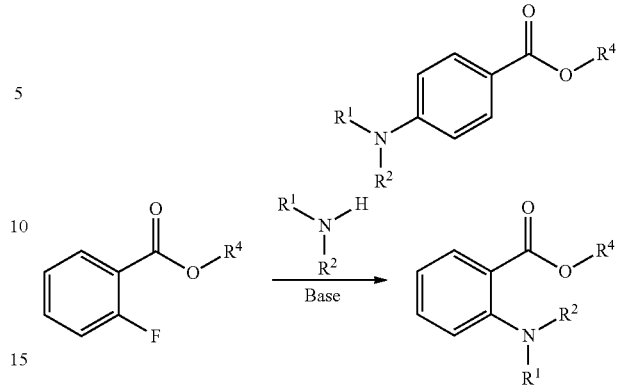

wherein $R^1$ and $R^2$ independently represent methyl or ethyl groups and $R^4$ represents any substituent.

Surprisingly, the co-initiator mixtures prepared using these methods, including the compound according to Formula I, are found to be sufficiently soluble in acrylate resins to find broad applicability in UV-curing processes, whereas the individual components may not be sufficiently soluble to be useful on their own. Furthermore, the mixtures show high reactivity in spite of the high molecular weight of the components in the preferred examples of this invention.

Unless otherwise stated, each of the integers described may be used in combination with any other integer as would be understood by the person skilled in the art. Further, although all aspects of the invention preferably "comprise" the features described in relation to that aspect, it is specifically envisaged that they may "consist" or "consist essentially" of those features outlined in the claims. In addition, all terms, unless specifically defined herein, are intended to be given their commonly understood meaning in the art.

Further, in the discussion of the invention, unless stated to the contrary, the disclosure of alternative values for the upper or lower limit of the permitted range of a parameter, is to be construed as an implied statement that each intermediate value of said parameter, lying between the smaller and greater of the alternatives, is itself also disclosed as a possible value for the parameter.

In addition, unless otherwise stated, all numerical values appearing in this application are to be understood as being modified by the term "about".

The examples which follow relate to methods of preparation of preferred illustrations of the invention, and thereafter the results of relevant tests undertaken on the materials are described.

EXAMPLES

Materials

All materials used in the examples are readily available from standard commercial sources such as Sigma-Aldrich Company Ltd. and Tokyo Chemical Industry Ltd. unless otherwise specified.

Ethoxylated bisphenol A dimethacrylate (EO/phenol 10) and tripropyleneglycol diacrylate are available from Sartomer. Ebercryl 40 is available from Allnex.

Example 1: Synthesis of the Amine Co-initiator Components

Synthesis of 4-(Dimethylamino)benzoyl Chloride Hydrochloride

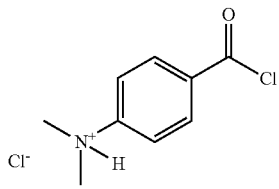

N,N-Dimethylformamide (7.0 mL, 91.0 mmol) was added at room temperature to a stirred suspension of 4-dimethylaminobenzoic acid (300 g, 1.82 mol) in toluene (1.5 L) and the mixture was heated to 65° C. Thionyl chloride (158 mL, 2.18 mol) was added at this temperature over approx. 1.5 h and the reaction mixture was heated at 60-65° C. for a further 5 h. During this time the starting material dissolved, giving a biphasic orange solution. Analysis by HPLC indicated that this stage of the reaction was complete. Concentration under reduced pressure gave the acid chloride as a mixture of the hydrochloride salt and the free amine, which was used immediately in the next step.

Synthesis of Amine AC1 (Compound of Formula I-a)

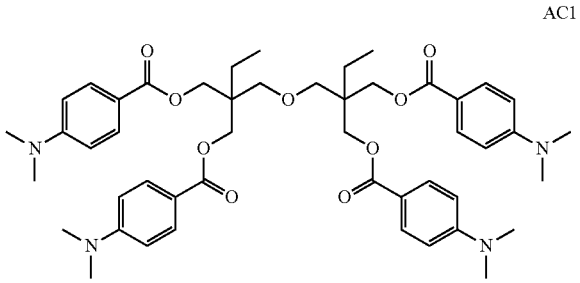

Triethylamine (508 mL, 3.64 mol) was added over 30 minutes at room temperature to a stirred suspension of 4-(dimethylamino)benzoyl chloride hydrochloride (1.82 mol) in toluene (2.5 L). Di-(trimethylolpropane) (118 g, 0.473 mol) was added in one portion and the mixture was heated to 85° C. for 16 h. The mixture was allowed to cool to room temperature and water (1 L) was added. The layers were separated and the organic layer was washed with water (2×500 mL), saturated sodium bicarbonate solution (500 mL) and brine (500 mL). The organic phase was dried (MgSO$_4$), concentrated and dried thoroughly under reduced pressure to give the crude product as a pale cream-coloured solid (368 g, 96%). Recrystallisation of a portion of the solid (30 g) from boiling ethyl acetate (150 mL) gave the pure product as a colourless solid, which was re-dissolved in dichloromethane (100 mL), concentrated under reduced pressure and dried thoroughly under vacuum, giving the pure product AC1. $^1$H NMR (400 MHz, CDCl$_3$); 7.87 (d, J=9.0 Hz, 8H), 6.59 (d, J=9.0 Hz, 8H), 4.32 (d, J=1.5 Hz, 8H), 3.51 (s, 4H), 3.01 (s, 24H), 1.62 (q, J=7.5 Hz, 4H), 0.91 (t, J=7.5 Hz, 6H).

Synthesis of Amine AC2 (Compound of Formula II)

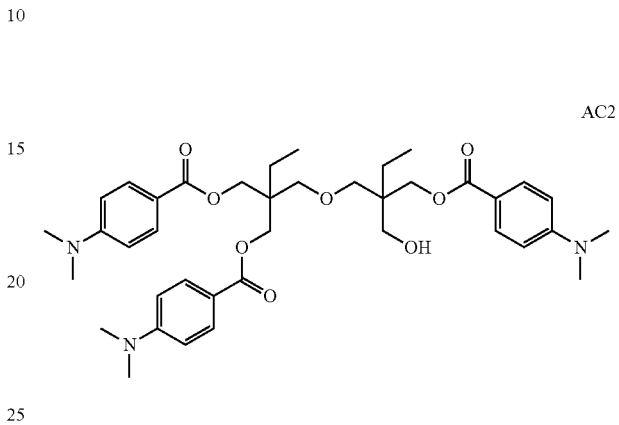

Triethylamine (42.4 mL, 303 mmol) was added over 10 minutes at room temperature to a stirred suspension of 4-(dimethylamino)benzoyl chloride hydrochloride (151 mmol) in toluene (125 mL). Di-(trimethylolpropane) (12.6 g, 50.5 mmol) was added in one portion and the mixture was heated to 85° C. for 16 h. The mixture was allowed to cool to room temperature and water (50 mL) was added. The layers were separated and the organic layer was washed with water (2×50 mL), saturated sodium bicarbonate solution (50 mL) and brine (50 mL). The organic phase was dried (MgSO$_4$) and concentrated under reduced pressure to give the crude product. Purification by column chromatography (eluting with 50:1 dichloromethane-methanol) gave the pure product AC2 as a colourless solid (4.7 g, 13%). $^1$H NMR (400 MHz, CDCl$_3$); 7.98-7.66 (m, 6H), 6.73-6.49 (m, 6H), 4.45-4.15 (m, 6H), 3.62-3.28 (m, 6H), 3.02 (s, 18H), 1.62 (q, J=7.5. Hz, 2H), 1.46 (q, J=7.5 Hz, 2H), 0.96 (t, J=7.5 Hz, 3H), 0.86 (t, J=7.5 Hz, 3H).

Synthesis of Amine AC3 (Compound of Formula III)

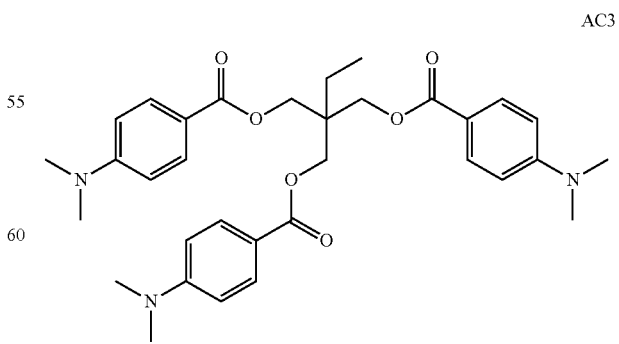

Triethylamine (17.0 mL, 121 mmol) was added over 5 minutes at room temperature to a stirred suspension of 4-(dimethylamino)benzoyl chloride hydrochloride (60.6 mmol) in toluene (50 mL). Trimethylolpropane (2.85 g, 21.3 mmol) was added in one portion and the mixture was heated to 90° C. for 16 h. The mixture was allowed to cool to room temperature and water (50 mL) was added. The layers were separated and the organic layer was washed with water (2×50 mL), saturated sodium bicarbonate solution (50 mL) and brine (50 mL). The organic phase was dried (MgSO$_4$) and concentrated under reduced pressure to give the crude product. Recrystallisation from 6:1 ethyl acetate-toluene (70 mL) gave the pure product as a pale cream-coloured solid (6.2 g, 51%), which was re-dissolved in dichloromethane (50 mL), concentrated under reduced pressure and dried thoroughly under vacuum, giving the pure product AC3. $^1$H NMR (400 MHz, CDCl$_3$): 7.87 (d, J=9.0 Hz, 6H), 6.60 (d, J=9.0 Hz, 6H), 4.41 (s, 6H), 3.01 (s, 18H), 1.72 (q, J=7.5 Hz, 2H), 0.99 (t, J=7.5 Hz, 3H).

Synthesis of Amine AC4 (Compound of Formula IV)

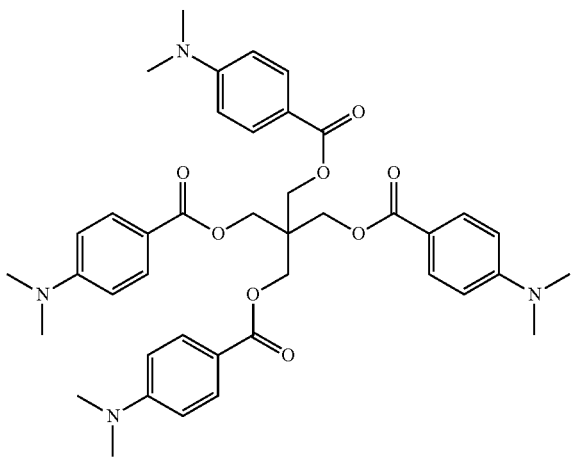

AC4

Triethylamine (17.0 mL, 121 mmol) was added over 5 minutes at room temperature to a stirred suspension of 4-(dimethylamino)benzoyl chloride hydrochloride (60.6 mmol) in toluene (50 mL). Pentaerythritol (2.15 g, 15.8 mmol) was added in one portion and the mixture was heated to 90° C. for 16 h, during which time a solid precipitated. The mixture was allowed to cool to room temperature and tert-butyl methyl ether (70 mL) was added. The solid was collected by filtration and washed with water (100 mL), methanol (100 mL) and tert-butyl methyl ether (50 mL), giving the crude product. Recrystallisation from boiling acetonitrile gave the pure product as a cream-coloured solid (7.1 g, 62%) which was re-dissolved in dichloromethane (50 mL), concentrated under reduced pressure and dried thoroughly under vacuum, giving the pure product AC4. $^1$H NMR (400 MHz, CDCl$_3$); 7.88 (d, J=9.0 Hz, 8H), 6.58 (d, J=9.0 Hz, 8H), 4.62 (s, 8H), 3.00 (s, 24H).

Synthesis of Amine AC5 (Compound of Formula V)

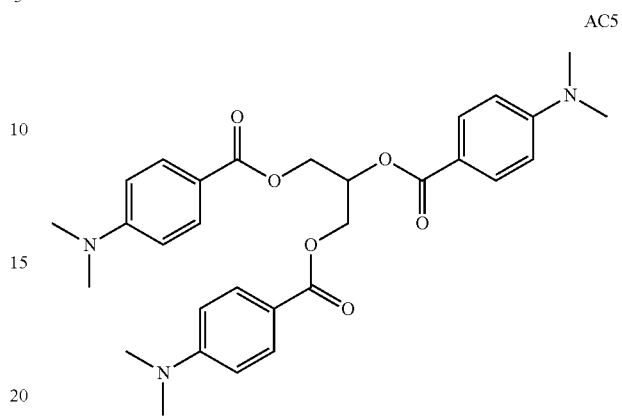

AC5

Triethylamine (8.5 mL, 60.6 mmol) was added over 5 minutes at room temperature to a stirred suspension of 4-(dimethylamino)benzoyl chloride hydrochloride (30.3 mmol) in toluene (25 mL). Glycerol (0.85 g, 9.23 mmol) was added in one portion and the mixture was heated to 90° C. for 16 h. The mixture was allowed to cool to room temperature and saturated sodium bicarbonate solution (50 mL) was added. The layers were separated and the organic layer was washed with saturated sodium bicarbonate solution (50 mL), water (50 mL) and brine (50 mL). The organic phase was dried (MgSO$_4$) and concentrated under reduced pressure to give the crude product. Recrystallisation from boiling acetonitrile gave the pure product as a pale cream-coloured solid. (1.28 g, 26%), which was re-dissolved in dichloromethane (30 mL), concentrated under reduced pressure and dried thoroughly under vacuum, giving the pure product AC5. $^1$H NMR (400 MHz, CDCl$_3$); 7.95-7.90 (m, 6H), 6.63-6.61 (m, 6H), 5.74 (p, J=5.0 Hz, 1H), 4.62 (qd, J=12.0 and 5.0 Hz, 4H), 3.02 (s, 18H).

Example 2: Preparation of Co-Initiator Mixtures

Preparation of Amine Mixture AM1

An 82:18 mixture of AC1 and AC2 respectively:

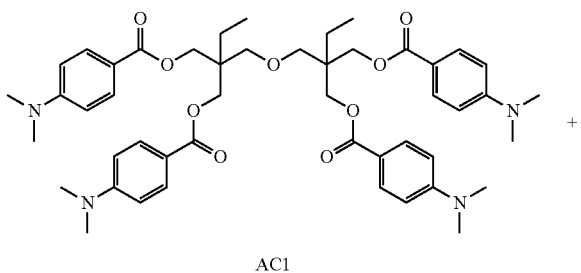

AC1

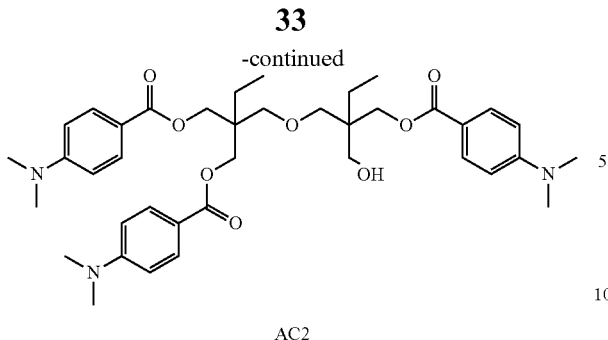

AC2

Triethylamine (508 mL, 3.64 mol) was added over 30 minutes at room temperature to a stirred suspension of 4-(dimethylamino)benzoyl chloride hydrochloride (1.82 mol) in toluene (2.5 L). Di-(trimethylolpropane) (118 g, 0.473 mol) was added in one portion and the mixture was heated to 85° C. for 16 h. The mixture was allowed to cool to room temperature and water (1 L) was added. The layers were separated and the organic layer was washed with water (2×500 mL), saturated sodium bicarbonate solution (500 mL) and brine (500 mL). The organic phase was dried (MgSO$_4$), concentrated and dried thoroughly under reduced pressure to give the product as a pale cream-coloured solid, containing an approx. 82:18 ratio (by HPLC area %) of the two products AC1 and AC2 (368 g, 96% yield).

Preparation of Amine Mixture AM2

A 50:50 w/w mixture of AC1 and AC2 respectively: the pure solid amines AC1 and AC2 were combined in proportion to give a 50:50 w/w mixture and the solid mixture was dissolved in dichloromethane, giving a homogenous solution. The solvent was removed on a rotary evaporator in vacuo and the resulting solid was thoroughly dried under vacuum, giving the mixture AM2.

Preparation of Amine Mixture AM3

A 25:75 w/w mixture of AC1 and AC2 respectively: the pure solid amines AC1 and AC2 were combined in proportion to give a 25:75 w/w mixture and the solid mixture was dissolved in dichloromethane, giving a homogenous solution. The solvent was removed on a rotary evaporator in vacuo and the resulting solid was thoroughly dried under vacuum, giving the mixture AM3.

Preparation of Amine Mixture AM4

An 85:15 w/w mixture of AC1 and AC3 respectively: the pure solid amines AC1 and AC3 were combined in proportion to give an 85:15 w/w mixture and the solid mixture was dissolved in dichloromethane, giving a homogenous solution. The solvent was removed on a rotary evaporator in vacuo and the resulting solid was thoroughly dried under vacuum, giving the mixture AM4.

Preparation of Amine Mixture AM5

An 85:15 w/w mixture of AC1 and AC4 respectively: the pure solid amines AC1 and AC4 were combined in proportion to give an 85:15 w/w mixture and the solid mixture was dissolved in dichloromethane, giving a homogenous solution. The solvent was removed on a rotary evaporator in vacuo and the resulting solid was thoroughly dried under vacuum, giving the mixture AM5.

Preparation of Amine Mixture AM6

An 85:15 w/w mixture of AC1 and AC5 respectively: the pure solid amines AC1 and AC5 were combined in proportion to give an 85:15 w/w mixture and the solid mixture was dissolved in dichloromethane, giving a homogenous solution. The solvent was removed on a rotary evaporator in vacuo and the resulting solid was thoroughly dried under vacuum, giving the mixture AM6.

Example 3: Solubility Experiments

This example illustrates the improved solubility of the co-initiator mixtures compared to single component amine co-initiator compositions, illustrating the benefit of providing a composition comprising both the compound of Formula I and the ancillary amine. For comparison, the solubility of amine mixtures as provided by this invention, of which mixtures AM1-AM6 are representative examples, were tested alongside single component formulations comprising only the amines AC1-AC5.

Mixtures of amine synergists were prepared using one of the methods described above.

The solid amines AC1-AC5 or mixtures of amines AM1-AM6 were added portion-wise in 1% w/w portions to stirred 5.0 g samples of the following acrylate resins and the samples were stirred at 15-20° C. until all solid material was completely dissolved: HDDA (1,6-hexanediol diacrylate), TMPTA (trimethylolpropane triacrylate), TPGDA (tripropyleneglycol diacrylate). At the concentrations given below (Table 2a-2k) all solids remained in solution for at least 7 days at 15-20° C. unless otherwise stated. In cases where the solids began to crystallise out of solution within this time the mixtures were warmed to approx. 40° C. to re-dissolve the solids and the concentrations were adjusted to the given values by the addition of extra resin, whereupon the solids remained dissolved at the adjusted concentration for at least 7 days at 15-20° C. Solubility above 10% w/w was not tested in any case. The weight % is based on the total weight of the mixture.

TABLE 2a

| Amine Co-initiator AC1 | |
| --- | --- |
| Acrylate | Solubility (% w/w at ~15-20° C.) |
| HDDA | 5 |
| TMPTA | 4 |
| TPGDA | 3 |

TABLE 2b

| Amine Co-initiator AC2 | |
| --- | --- |
| Acrylate | Solubility (% w/w at ~15-20° C.) |
| HDDA | 10 |
| TMPTA | 10 |
| TPGDA | 10 |

TABLE 2c

| Amine Co-initiator AC3 | |
| --- | --- |
| Acrylate | Solubility (% w/w at ~15-20° C.) |
| HDDA | <2 |
| TMPTA | <2 |
| TPGDA | <2 |

Though the solid material initially dissolved at 2% w/w, it crystallised out of all three resins within 24 h.

TABLE 2d

| Amine Co-initiator AC4 | |
| --- | --- |
| Acrylate | Solubility (% w/w at ~15-20° C.) |
| HDDA | <1 |
| TMPTA | <1 |
| TPGDA | <1 |

The solid material would not dissolve at 1% w/w.

TABLE 2e

| Amine Co-Initiator AC5 | |
| --- | --- |
| Acrylate | Solubility (% w/w at ~15-20° C.) |
| HDDA | <1 |
| TMPTA | <1 |
| TPGDA | <1 |

The solid material would not dissolve at 1% w/w.

TABLE 2f

| Amine Mixture AM1 | |
| --- | --- |
| Acrylate | Solubility (% w/w at ~15-20° C.) |
| HDDA | 10 |
| TMPTA | 10 |
| TPGDA | 7 |

TABLE 2g

| Amine Mixture AM2 | |
| --- | --- |
| Acrylate | Solubility (% w/w at ~15-20° C.) |
| HDDA | 10 |
| TMPTA | 10 |
| TPGDA | 10 |

TABLE 2h

| Amine Mixture AM3 | |
| --- | --- |
| Acrylate | Solubility (% w/w at ~15-20° C.) |
| HDDA | 10 |
| TMPTA | 10 |
| TPGDA | 10 |

TABLE 2i

| Amine Mixture AM4 | |
| --- | --- |
| Acrylate | Solubility (% w/w at ~15-20° C.) |
| HDDA | 6 |
| TMPTA | 6 |
| TPGDA | 4 |

TABLE 2j

| Amine Mixture AM5 | |
| --- | --- |
| Acrylate | Solubility (% w/w at ~15-20° C.) |
| HDDA | 5 |
| TMPTA | 6 |
| TPGDA | 3 |

TABLE 2k

| Amine Mixture AM6 | |
| --- | --- |
| Acrylate | Solubility (% w/w at ~15-20° C.) |
| HDDA | 6 |
| TMPTA | 6 |
| TPGDA | 4 |

Surprisingly, the amine mixtures AM1-AM6 exhibit better solubility in the acrylate resins than most of the pure amine co-initiators AC1-AC5, and are comparable to AC2 alone.

Example 4: Curing Experiments

The following example illustrates the high curing speed of co-initiators which contain the compound of Formula I and the ancillary amine. For comparison, the commercially available amine co-initiators SpeedCure EDB (Lambson Limited) and diffusion-hindered polymeric amine SpeedCure 7040 (Lambson Limited) were also tested. Additionally, the pure amines AC1-AC5 were tested alongside the mixtures provided by this invention, of which the mixtures AM1-AM6 are representative examples.

The amine co-initiators or co-initiator mixtures (0.20 g) were added to a resin mixture (4.0 g) containing 1% w/w SpeedCure 2-ITX (Lambson Limited) and 4% w/w SpeedCure BP (Lambson Limited) in 70:30 ethoxylated bisphenol A dimethacrylate (EO/phenol 10):trimethylolpropane triacrylate with stirring at 15-20° C. until all solid material had dissolved. In cases where the solid amines would not dissolve, these formulations were not tested.

Formulations were cured at 6 and 24 μm film thicknesses under Hg lamp using a Dymax curing instrument with approx. 16 m/min belt speed. The number of passes under the lamp required to give a 'tack-free' (TF) coating (as determined when the surface of the coating no longer feels sticky when lightly touched) or full cure as determined by the 'thumb-twist' test (TT) (i.e. until no visible mark is made when a thumb is pressed down firmly onto the coating with a twisting motion) are given in Table 3.

TABLE 3

| Amine or Mixture | No. of Passes Required | | | |
|---|---|---|---|---|
| | 6 μm | | 24 μm | |
| | TF | TT | TF | TT |
| None | No cure * | No cure * | 20 | 26 |
| SpeedCure EDB | 1 | 6 | 1 | 2 |
| SpeedCure 7040 | 2 | 10 | 1 | 3 |
| AC1 | 1 | 5 | 1 | 2 |
| AC2 | 1 | 6 | 1 | 2 |
| AC3 ** | — | — | — | — |
| AC4 ** | — | — | — | — |
| AC5 ** | — | — | — | — |
| AM1 | 1 | 5 | 1 | 2 |
| AM2 | 1 | 6 | 1 | 2 |
| AM3 | 1 | 6 | 1 | 2 |
| AM4 | 1 | 5 | 1 | 2 |
| AM5 | 1 | 5 | 1 | 2 |
| AM6 | 1 | 5 | 1 | 2 |

* No cure after 30 passes under the lamp
** The amines would not dissolve in the formulation and so these formulations were not tested.

Evidently all of the amine mixtures AM1-AM6 are effective amine co-initiators for promoting rapid UV-curing under these conditions. The mixtures exhibit comparable reactivity to SpeedCure EDB and are much more reactive than the diffusion-hindered polymeric amine co-initiator SpeedCure 7040. Surprisingly, the relatively high molecular weights of the amines present in the mixtures AM1-AM6 do not inversely affect their performance as co-initiators compared to the smaller molecule SpeedCure EDB. The amines AC3-AC5 were not sufficiently soluble in the acrylate resin formulation to be tested, but the amine mixtures AM1-AM6 were fully dissolved at this concentration.

Example 5: Migration Experiments

The following example illustrates the potential to use a mixture of amine co-initiators as defined by this invention as a low-migration co-initiator system.

Figure 2:
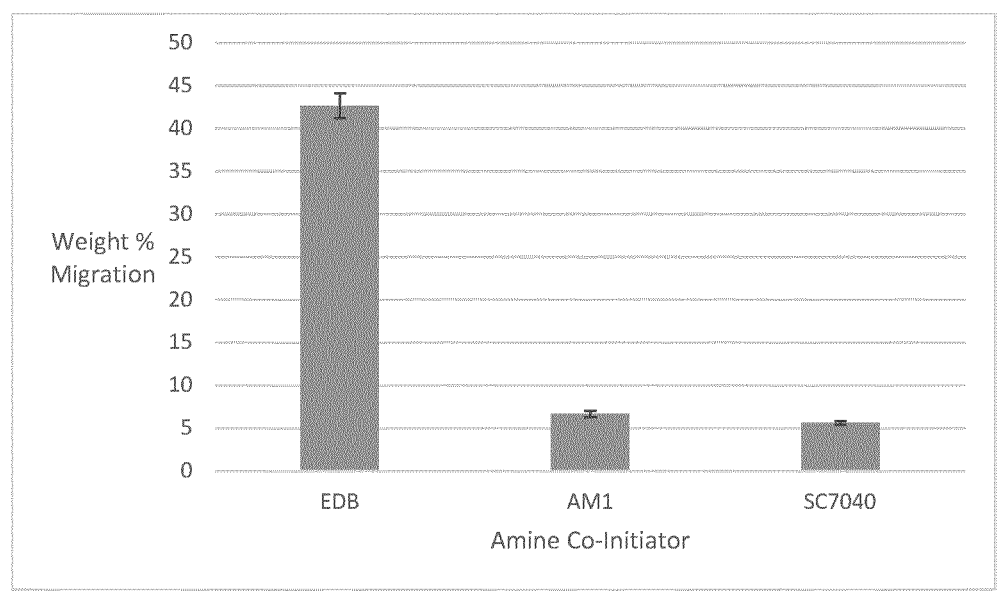
FIG. 2 illustrates the migration of amine co-initiators (the amines SpeedCure EDB and SpeedCure 7040, and mixture AM1) into 50% v/v ethanol in de-ionised water, 60° C. for 10 days, average of three runs (standard deviations included).
Figure 3:
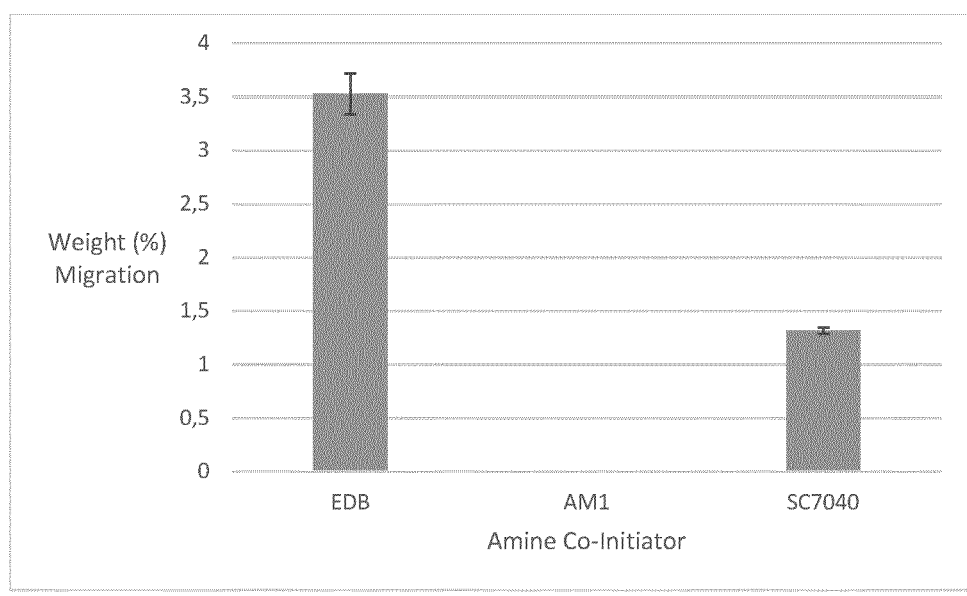
FIG. 3 illustrates the migration of amine co-initiators (the amines SpeedCure EDB and SpeedCure 7040, and mixture AM1) into 3% w/v acetic acid in de-ionised water, 60° C. for 10 days, average of three runs (standard deviations included).

Formulations containing 90% w/w Ebecryl 40 (Allnex), 4% w/w SpeedCure BP (Lambson Limited), 1% w/w SpeedCure 2-ITX (Lambson Limited) and 5% w/w of either SpeedCure EDB, SpeedCure 7040 (Lambson Limited) or the amine co-initiator mixture AM1 were cured onto paper strips in 24 μm films under a Hg lamp until fully cured (as determined by the 'thumb-twist' test, see Example 3). The cured paper strips were each cut to a size of approx. 100 cm 2 and the mass of cured resin adhered to each piece of paper was recorded. The cured paper strips were each submerged into 15 mL of solvent in sealed pressure vessels and were held at 60° C. in an oven for 10 days; the solvents used were either acetonitrile, 50% v/v ethanol in water, or 3% w/v acetic acid in water. All of the vessels were subsequently allowed to cool to 20-25° C. and the paper strips were removed from the simulant solvents. Samples of each solvent were filtered and injected onto HPLC, and all components dissolved in the solvents were eluted using appropriate HPLC methods. Comparison of peak areas to previously prepared calibration curves allowed for the masses of the amine co-initiators present in the injected volume of solvent to be calculated, and therefore also the total amount of amine dissolved in the 15 mL of simulant solvent for each sample. Since SpeedCure 7040 and mixture AM1 contain multiple components, the peak areas of all components in those mixtures were added together. The total amount of amine which had migrated from the cured films into the simulant solvents is expressed in Tables 4-6 and FIGS. 1-3 as a percentage of the total amount amine present on each cured strip (taken to be 5% of the total amount of cured resin on the strip). All experiments were performed in triplicate, and the mean was taken of the results for each amine. SpeedCure 2-ITX and SpeedCure BP were also seen to migrate from the cured films into the surrounding solvents in every case (along with other minor impurities), but these were not quantified.

TABLE 4

Migration of Amine Co-Initiators into Acetonitrile, 60° C. for 10 days, Average of Three Runs

| Amine Co-Initiator | Weight % of Amine Migrated |
|---|---|
| SpeedCure EDB | 47.5 |
| Amine Mixture AM1 | 15.6 |
| SpeedCure 7040 | 6.3 |

TABLE 5

Migration of Amine Co-Initiators into 50% v/v Ethanol in De-ionised Water, 60° C. for 10 days, Average of Three Runs

| Amine Co-Initiator | Weight % of Amine Migrated |
|---|---|
| SpeedCure EDB | 42.6 |
| Amine Mixture AM1 | 6.6 * |
| SpeedCure 7040 | 5.6 ** |

* Some of the co-initiator mixture AM1 was converted to ethyl (4-dimethylamino) benzoate by the conditions of the test (<0.5%); this was detected in the solvent and quantified by HPLC. This quantity is included in the total migration percentage given. 4-Dimethylaminobenzoic acid was also detected (approx. <0.5% of the total mass of co-initiator in the cured film), but this was not accurately quantified.
** This value includes ethyl (4-dimethylamino)benzoate, which is usually present in some quantity in Speedcure 7040, though some of the 7040 is also expected to have been converted to ethyl (4-dimethylamino)benzoate by the conditions of the test. 4-Dimethylaminobenzoic acid was not detected.

TABLE 6

Migration of Amine Co-Initiators into 3% w/v Acetic Acid in De-ionised Water, 60° C. for 10 days, Average of Three Runs

| Amine Co-Initiator | Weight % of Amine Migrated |
|---|---|
| SpeedCure EDB | 3.5 |
| Amine Mixture AM1 | <0.001 * |
| SpeedCure 7040 | 1.3 ** |

* Neither of the components of the mixture AM1 were detected in the solvent above this limit. 4-Dimethylaminobenzoic acid, a potential product of the hydrolysis of either of these components, was not detected.
** 4-Dimethylaminobenzoic acid was not detected.

In all cases the mixture of high molecular weight amine co-initiators AM1, a preferred example of this invention, migrated from the cured films into the surrounding solvents to a much lesser extent than the relatively low molecular weight co-initiator SpeedCure EDB. In the case of the food-simulant solvents aqueous ethanol and aqueous acetic acid (simulating alcoholic and acidic foodstuffs respectively), migration of the mixture AM1 was much lower than SpeedCure EDB, and no detectable quantity of either of the components of the mixture AM1 was detected in the aqueous acetic acid solvent system. In the ethanol/water solvent system the mixture AM1 had very similar migration properties to those of the polymeric amine co-initiator SpeedCure 7040, which has a higher average molecular weight, in spite of the fact that the mixture AM1 is not polymeric. This invention therefore provides a novel co-initiator system which not only has good solubility in acrylate resins, but also has similar migration properties to a commercial polymeric amine co-initiator, while also promoting significantly faster UV cure speed, as demonstrated in the previous example.

The invention claimed is:

1. A co-initiator mixture for use in UV curing comprising at least one aminobenzoate compound according to Formula I and at least one ancillary amine

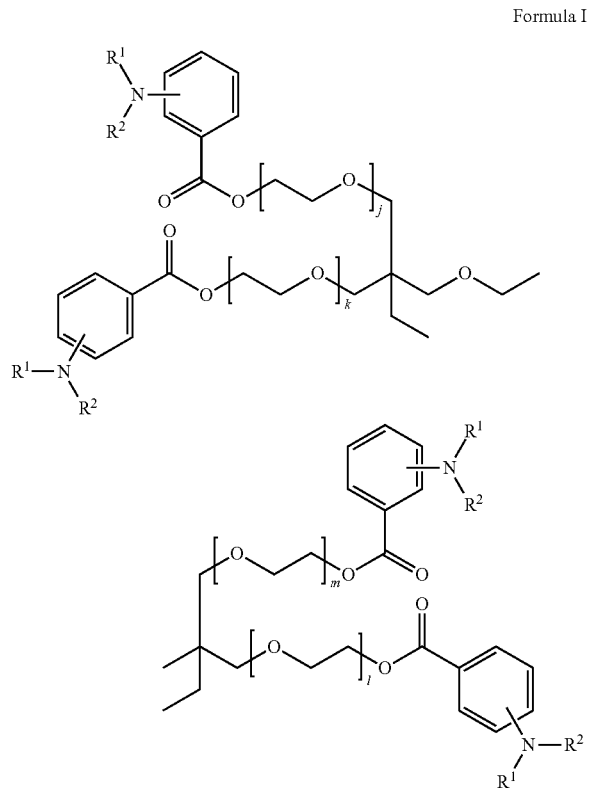

Formula I wherein in Formula I, $R^1$ and $R^2$ independently represent methyl or ethyl groups; and j, k, l and m independently represent integers from 0 to 20;

wherein the ancillary amine comprises at least one aminobenzoate derivative of different structure to the compound of Formula I.

2. The co-initiator of claim 1, wherein the percentage of the compound according to Formula I is in the range of 0.1 to 99.9 wt % based on the weight of the co-initiator mixture.

3. The co-initiator of claim 2, wherein the percentage of the compound according to Formula I is in the range of 5 to 95 wt % based on the weight of the co-initiator mixture.

4. The co-initiator of claim 3, wherein the percentage of the compound according to Formula I is in the range of 70 to 90 wt % based on the weight of the co-initiator mixture.

5. The co-initiator of claim 1, wherein $R^1$ and $R^2$ are methyl.

6. The co-initiator of claim 1, wherein the N,N-dialkylamino groups in Formula I are at the 4-position with respect to the ester groups.

7. The co-initiator of claim 1, wherein the compound according to Formula I has j, k, l, and m that are all equal to 0.

8. The co-initiator of claim 1, wherein the sum of j+k+l+m is from 1 to 30.

9. The co-initiator of claim 1, wherein the compound according to Formula I has the structure according to Formula I-a

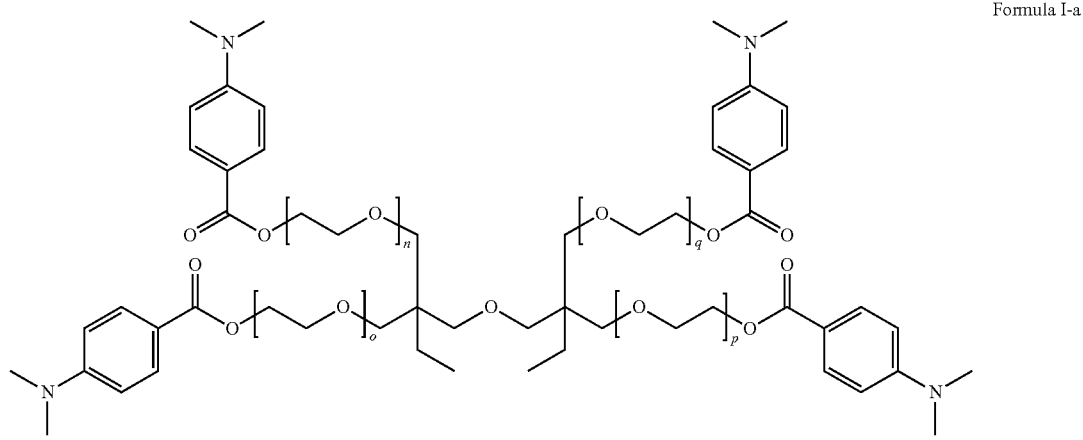

Formula I-a wherein n, o, p and q independently represent integers from 0 to 20.

10. The co-initiator of claim 9, wherein the compound according to Formula I-a has n, o, p and q that are all equal to 0.

11. The co-initiator of claim 9, wherein the sum of n+o+p+q is from 1 to 30.

12. The co-initiator of claim 1, wherein the ancillary amine comprises at least one N,N-dialkylaminobenzoate moiety according to formula (A)

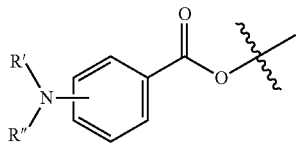

(A)

wherein R' and R" are independently alkyl.

13. The co-initiator of claim 12, wherein the N,N-dialkylaminobenzoate moiety of formula (A) has the —NR'R" group in para position with respect to the ester group.

14. The co-initiator of claim 1, wherein the ancillary amine comprises a compound according to Formula II

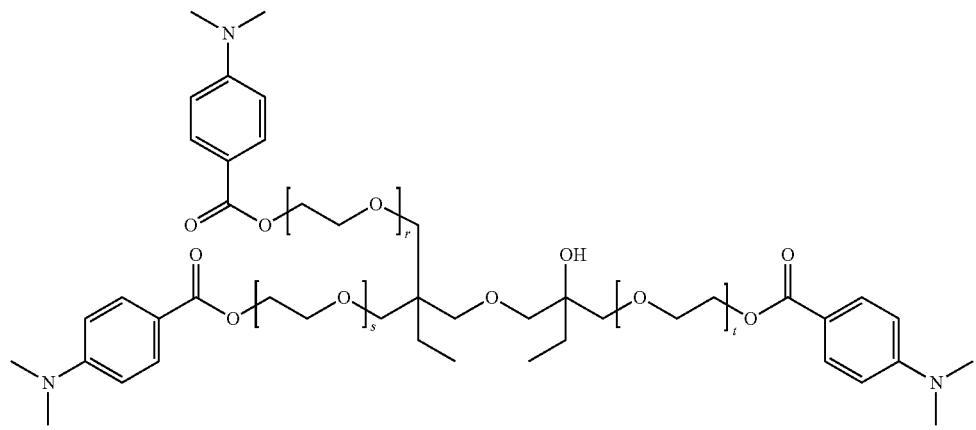

Formula II wherein r, s and t independently represent integers from 0 to 20.

15. The co-initiator of claim 1, wherein the ancillary amine comprises a compound according to Formula III

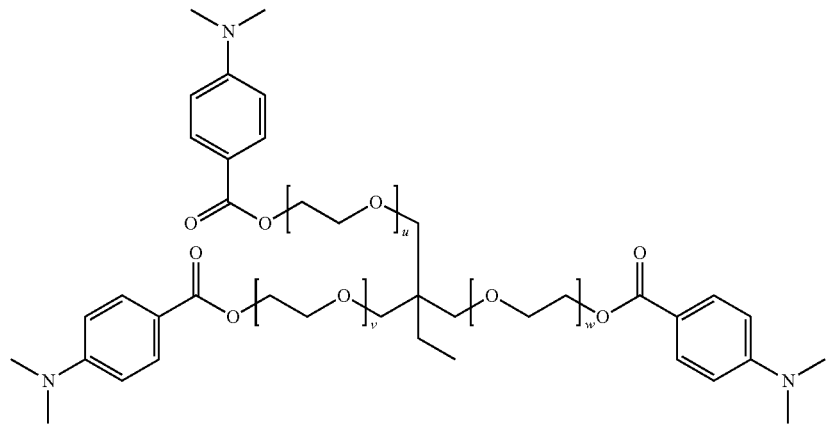

Formula III wherein u, v and w independently represent integers from 0 to 20.

16. The co-initiator of claim 1, wherein the ancillary amine comprises a compound according to Formula IV

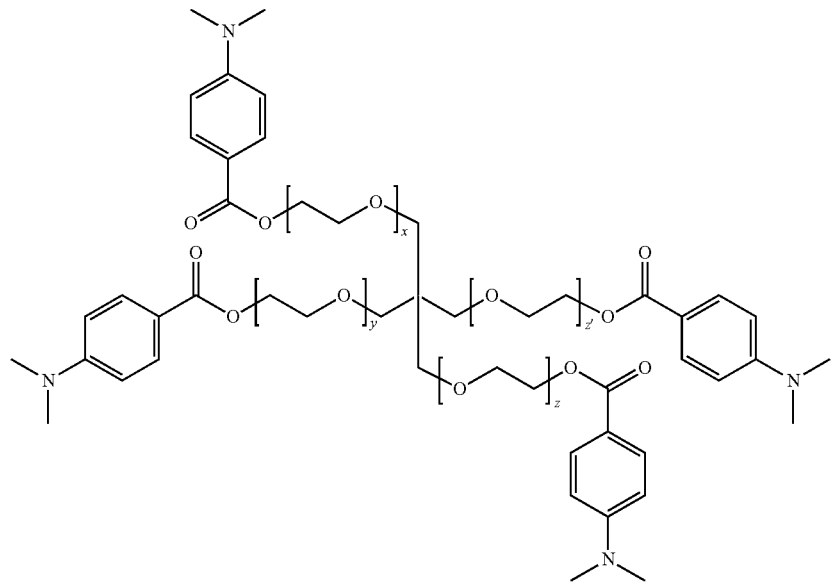

Formula IV wherein x, y, z and z' independently represent integers from 0 to 20.

17. The co-initiator of claim 1, wherein the ancillary amine comprises a compound according to Formula V

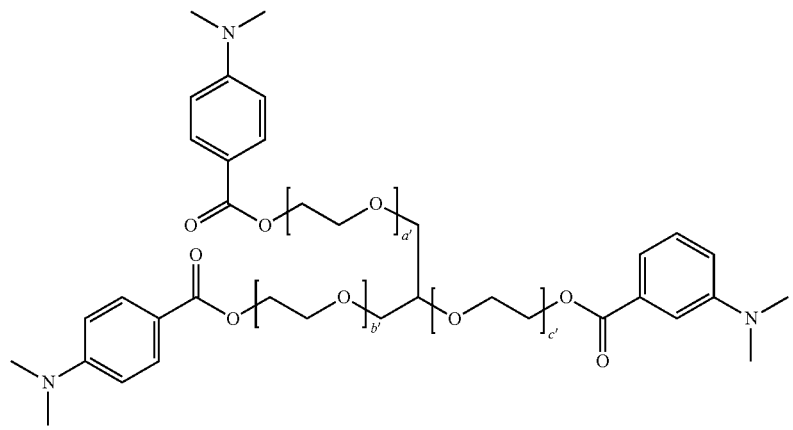

Formula V wherein a', b' and c' independently represent integers from 0 to 20.

18. A photoinitiator blend comprising the co-initiator of claim 1, and one or more Type-I or Type-II photoinitiators.

19. A radiation-curable composition comprising the co-initiator of claim 1, one or more Type-I or Type-II photoinitiators and one or more polymerisable monomers, oligomers or prepolymers.

20. The radiation-curable composition of claim 19, which is a UV-curable coating or ink.

21. The radiation-curable composition of claim 19 further comprising a colourant.

22. A cured material obtained by curing the radiation-curable composition of claim 19.

23. A low migration cured material, obtained by curing the radiation-curable composition of any one of claim 19.

24. The cured material of claim 23, wherein the cured material is an ink, lacquer or varnish.

* * * * *